(12) United States Patent
Sato et al.

(10) Patent No.: US 11,142,755 B2
(45) Date of Patent: Oct. 12, 2021

(54) MUTANT GLUTATHIONE SYNTHETASE AND METHOD FOR PRODUCING GAMMA-GLUTAMYL-VALYL-GLYCINE

(71) Applicant: AJINOMOTO CO., INC., Tokyo (JP)

(72) Inventors: Ayako Sato, Kawasaki (JP); Eri Higashiura, Kawasaki (JP); Misato Okamoto, Kawasaki (JP); Takayuki Ito, Kawasaki (JP); Erika Watanabe, Kawasaki (JP); Uno Tagami, Kawasaki (JP); Yuki Oda, Kawasaki (JP); Tatsuki Kashiwagi, Kawasaki (JP); Masayuki Sugiki, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 16/287,459

(22) Filed: Feb. 27, 2019

(65) Prior Publication Data

US 2019/0264191 A1 Aug. 29, 2019

(30) Foreign Application Priority Data

Feb. 27, 2018 (JP) .............................. JP2018-033217

(51) Int. Cl.
*C12P 21/02* (2006.01)
*C12N 9/00* (2006.01)

(52) U.S. Cl.
CPC ................ *C12N 9/93* (2013.01); *C12P 21/02* (2013.01); *C12Y 603/02003* (2013.01)

(58) Field of Classification Search
None
See application file for complete search history.

(56) References Cited

U.S. PATENT DOCUMENTS

| | | | |
|---|---|---|---|
| 2010/0105864 A1 | 4/2010 | Yoneda et al. | |
| 2010/0120698 A1 | 5/2010 | Nagasaki et al. | |
| 2010/0183792 A1 | 7/2010 | Nagasaki et al. | |
| 2010/0192985 A1* | 8/2010 | Aehle | C11D 3/386 134/26 |
| 2011/0046046 A1 | 2/2011 | Hara et al. | |
| 2011/0071075 A1 | 3/2011 | Takeuchi et al. | |
| 2014/0212920 A1 | 7/2014 | Nozaki et al. | |
| 2016/0326510 A1* | 11/2016 | Sasahara | C12P 21/02 |
| 2016/0340707 A1 | 11/2016 | Tsuji et al. | |
| 2018/0195103 A1 | 7/2018 | Sasahara et al. | |

FOREIGN PATENT DOCUMENTS

| | | |
|---|---|---|
| JP | 8-119916 A | 5/1996 |
| JP | 2012-85637 A | 5/2012 |
| WO | WO 2007/055388 A2 | 5/2007 |
| WO | WO 2007/055393 A1 | 5/2007 |
| WO | WO 2008/139945 A1 | 11/2008 |
| WO | WO 2008/139946 A1 | 11/2008 |
| WO | WO 2008/139947 A1 | 11/2008 |
| WO | WO 2009/107660 A1 | 9/2009 |
| WO | WO 2009/119554 A1 | 10/2009 |
| WO | WO 2013/051685 A1 | 4/2013 |
| WO | WO 2013/054447 A1 | 4/2013 |

OTHER PUBLICATIONS

UniProt Database Accession No. Q8UII5, Feb. 2017, 2 pages (Year: 2017).*
UniProt Database Accession No. E3G469, Feb. 2017, 2 pages (Year: 2017).*
UniProt Database Accession No. A0A069XH59, Feb. 2017, 2 pages (Year: 2017).*
Extended European Search Report issued Jul. 29, 2019 in Patent Application No. 19159393.8, 10 pages.
"Glutathione synthetase" Database UniParc [Online], Database accession No. UPI000BE3C332, https://www.uniprot.org/uniparc/UPI000BE3C332, XP002793010, 2017, 2 pages.
"Glutathione synthetase" Database UniParc [Online], Database accession No. UPI00069C5B4C, https://www.uniprot.org/uniparc/UPI00069C5B4C, XP002793011, 2015, 2 pages.
"Glutathione synthetase" Database UniParc [Online], Database accession No. UPI0002CB4AA2, https://www.uniprot.org/uniparc/UPI0002CB4AA2, XP002793009, 2013, 2 pages.
Hara, K.Y. et al. "Glutathione production by efficient ATP-regenerating *Escherichia coli* mutants" FEMS Microbiology Letters, vol. 297, XP055156313, 2009, pp. 217-224.
"Glutathione synthetase" Database UniParc [Online], Database accession No. UPI000E31F75F, https://www.uniprot.org/uniparc/UPI000E31F75F, XP002793013, 2018, 2 pages.
"Glutathione synthetase" Database UniParc [Online], Database accession No. UPI000DEBF624, https://www.uniprot.org/uniparc/UPI000DEBF624, XP002793014, 2018, 2 pages.
"Glutathione synthetase" Database UniParc [Online], Database accession No. UPI000D6A60D3, https://www.uniprot.org/uniparc/UPI000D6A60D3, XP002793012, 2018, 2 pages.
Tanaka, T., et al., "Mutational and Proteolytic Studies on a Flexible Loop in Glutathione Synthetase from *Escherichia coli* B: The Loop and Arginine 233 Are Critical for the Catalytic Reaction", Biochemistry, vol. 31 No. 8, 1992, pp. 2259-2265.
Tanaka, T., et al., "Flexibility Impaired by Mutations Revealed the Multifunctional Roles of the Loop in Glutathione Synthetase", Biochemistry, 1993, vol. 32 No. 46, pp. 12398-12404.
Tanaka, T., et al., "Nicked Multifunctional Loop of Glutathione Synthetase Still Protects the Catalytic Intermediate", Archives of Biochemistry and Biophysics, vol. 339 No. 1, Mar. 1, 1997, pp. 151-156.
Office action dated Aug. 24, 2021 in corresponding Japanese Patent Application No. 2018-033217 (with English machine translation).
Summary of the firty fifth protein structure lecture summary, 1994, p. 89-92 (documents showing well-known arts).

* cited by examiner (Continued)

*Primary Examiner* — David Steadman
(74) *Attorney, Agent, or Firm* — Oblon, McClelland, Maier & Neustadt, L.L.P.

(57) ABSTRACT

A mutant glutathione synthetase (GSHB) suitable for generating γ-Glu-Val-Gly, and a method for producing γ-Glu-Val-Gly using the same are provided. γ-Glu-Val-Gly is produced by using a mutant GSHB having a mutation at such a position as V7, N13, I14, N15, K17, F22, F95, M165, N199, Y200, P202, I274, T285, and P287.

22 Claims, 1 Drawing Sheet

Specification includes a Sequence Listing.

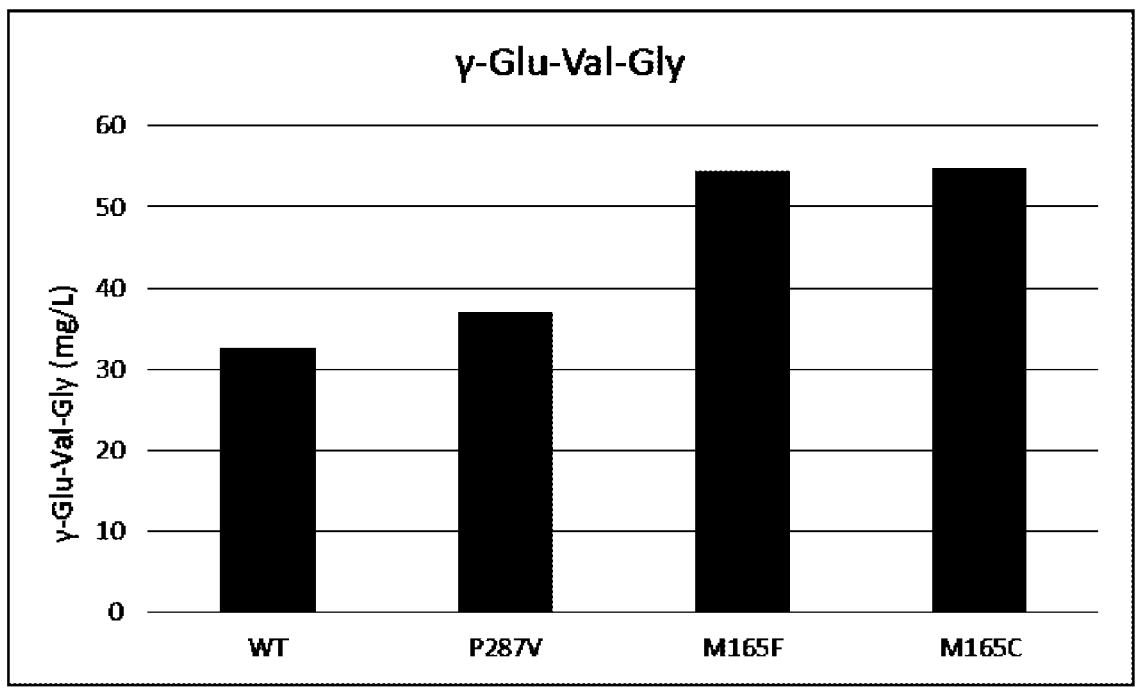

SEQUENCE LISTING

```
<160> NUMBER OF SEQ ID NOS: 30

<210> SEQ ID NO 1
<211> LENGTH: 951
<212> TYPE: DNA
<213> ORGANISM: Escherichia coli

<400> SEQUENCE: 1
atgatcaagc tcggcatcgt gatggacccc atcgcaaaca tcaacatcaa gaaagattcc      60
agttttgcta tgttgctgga agcacagcgt cgtggttacg aacttcacta tatggagatg     120
ggcgatctgt atctgatcaa tggtgaagcc cgcgcccata cccgcacgct gaacgtgaag     180
```

```
cagaactacg aagagtggtt ttcgttcgtc ggtgaacagg atctgccgct ggccgatctc    240
gatgtgatcc tgatgcgtaa agacccgccg tttgataccg agtttatcta cgcgacctat    300
attctggaac gtgccgaaga gaaagggacg ctgatcgtta caagccgca gagcctgcgc    360 gactgtaacg agaaactgtt taccgcctgg ttctctgact taacgccaga aacgctggtt    420
acgcgcaata agcgcagct aaaagcgttc tgggagaaac acagcgacat cattcttaag    480
ccgctggacg gtatgggcgg cgcgtcgatt ttccgcgtga agaaggcga tccaaacctc    540 ggcgtgattg ccgaaaccct gactgagcat ggcactcgct actgcatggc gcaaaattac    600
ctgccagcca ttaaagatgg cgacaaacgc gtgctggtgg tggatggcga gccggtaccg    660
tactgcctgg cgcgtattcc gcaggggggc gaaacccgtg gcaatctggc tgccggtggt    720
cgcggtgaac tcgtccgct gacggaaagt gactggaaaa tcgcccgtca gatcgggccg    780
acgctgaaag aaaagggct gattttgtt ggtctggata tcatcggcga ccgtctgact    840
gaaattaacg tcaccagccc aacctgtatt cgtgagattg aagcagagtt tccggtgtcg    900
atcaccggaa tgttaatgga tgccatcgaa gcacgtttac agcagcagta a             951

<210> SEQ ID NO 2
<211> LENGTH: 316
<212> TYPE: PRT
<213> ORGANISM: Escherichia coli

<400> SEQUENCE: 2

Met Ile Lys Leu Gly Ile Val Met Asp Pro Ile Ala Asn Ile Asn Ile
1               5                   10                  15

Lys Lys Asp Ser Ser Phe Ala Met Leu Leu Glu Ala Gln Arg Arg Gly
            20                  25                  30

Tyr Glu Leu His Tyr Met Glu Met Gly Asp Leu Tyr Leu Ile Asn Gly
        35                  40                  45

Glu Ala Arg Ala His Thr Arg Thr Leu Asn Val Lys Gln Asn Tyr Glu
    50                  55                  60

Glu Trp Phe Ser Phe Val Gly Glu Gln Asp Leu Pro Leu Ala Asp Leu
65                  70                  75                  80

Asp Val Ile Leu Met Arg Lys Asp Pro Pro Phe Asp Thr Glu Phe Ile
                85                  90                  95

Tyr Ala Thr Tyr Ile Leu Glu Arg Ala Glu Glu Lys Gly Thr Leu Ile
            100                 105                 110

Val Asn Lys Pro Gln Ser Leu Arg Asp Cys Asn Glu Lys Leu Phe Thr
        115                 120                 125

Ala Trp Phe Ser Asp Leu Thr Pro Glu Thr Leu Val Thr Arg Asn Lys
    130                 135                 140

Ala Gln Leu Lys Ala Phe Trp Glu Lys His Ser Asp Ile Ile Leu Lys
145                 150                 155                 160

Pro Leu Asp Gly Met Gly Gly Ala Ser Ile Phe Arg Val Lys Glu Gly
                165                 170                 175

Asp Pro Asn Leu Gly Val Ile Ala Glu Thr Leu Thr Glu His Gly Thr
            180                 185                 190

Arg Tyr Cys Met Ala Gln Asn Tyr Leu Pro Ala Ile Lys Asp Gly Asp
        195                 200                 205

Lys Arg Val Leu Val Val Asp Gly Glu Pro Val Pro Tyr Cys Leu Ala
    210                 215                 220

Arg Ile Pro Gln Gly Gly Glu Thr Arg Gly Asn Leu Ala Ala Gly Gly
225                 230                 235                 240
```

Arg Gly Glu Pro Arg Pro Leu Thr Glu Ser Asp Trp Lys Ile Ala Arg
                245                 250                 255

Gln Ile Gly Pro Thr Leu Lys Glu Lys Gly Leu Ile Phe Val Gly Leu
        260                 265                 270

Asp Ile Ile Gly Asp Arg Leu Thr Glu Ile Asn Val Thr Ser Pro Thr
        275                 280                 285

Cys Ile Arg Glu Ile Glu Ala Glu Phe Pro Val Ser Ile Thr Gly Met
    290                 295                 300

Leu Met Asp Ala Ile Glu Ala Arg Leu Gln Gln Gln
305                 310                 315

<210> SEQ ID NO 3
<211> LENGTH: 27
<212> TYPE: DNA
<213> ORGANISM: Artificial Sequence
<220> FEATURE:
<223> OTHER INFORMATION: Synthetic primer

<400> SEQUENCE: 3
accagcgtga cctgtattcg tgagatt                                      27

<210> SEQ ID NO 4
<211> LENGTH: 27
<212> TYPE: DNA
<213> ORGANISM: Artificial Sequence
<220> FEATURE:
<223> OTHER INFORMATION: Synthetic primer

<400> SEQUENCE: 4
acaggtcacg ctggtgacgt taatttc                                      27

<210> SEQ ID NO 5
<211> LENGTH: 27
<212> TYPE: DNA
<213> ORGANISM: Artificial Sequence
<220> FEATURE:
<223> OTHER INFORMATION: Synthetic primer

<400> SEQUENCE: 5
gacggttgcg gcggcgcgtc gattttc                                      27

<210> SEQ ID NO 6
<211> LENGTH: 27
<212> TYPE: DNA
<213> ORGANISM: Artificial Sequence
<220> FEATURE:
<223> OTHER INFORMATION: Synthetic primer

<400> SEQUENCE: 6
gccgccgcaa ccgtccagcg gcttaag                                      27

<210> SEQ ID NO 7
<211> LENGTH: 27
<212> TYPE: DNA
<213> ORGANISM: Artificial Sequence
<220> FEATURE:
<223> OTHER INFORMATION: Synthetic primer

<400> SEQUENCE: 7
gacggttttg gcggcgcgtc gattttc                                      27

<210> SEQ ID NO 8
<211> LENGTH: 27
<212> TYPE: DNA

```
<213> ORGANISM: Artificial Sequence
<220> FEATURE:
<223> OTHER INFORMATION: Synthetic primer

<400> SEQUENCE: 8
gccgccaaaa ccgtccagcg gcttaag                                           27

<210> SEQ ID NO 9
<211> LENGTH: 27
<212> TYPE: DNA
<213> ORGANISM: Artificial Sequence
<220> FEATURE:
<223> OTHER INFORMATION: Synthetic primer

<400> SEQUENCE: 9
gacggttggg gcggcgcgtc gattttc                                           27

<210> SEQ ID NO 10
<211> LENGTH: 27
<212> TYPE: DNA
<213> ORGANISM: Artificial Sequence
<220> FEATURE:
<223> OTHER INFORMATION: Synthetic primer

<400> SEQUENCE: 10
gccgccccaa ccgtccagcg gcttaag                                           27

<210> SEQ ID NO 11
<211> LENGTH: 27
<212> TYPE: DNA
<213> ORGANISM: Artificial Sequence
<220> FEATURE:
<223> OTHER INFORMATION: Synthetic primer

<400> SEQUENCE: 11
gacggtgcgg gcggcgcgtc gattttc                                           27

<210> SEQ ID NO 12
<211> LENGTH: 27
<212> TYPE: DNA
<213> ORGANISM: Artificial Sequence
<220> FEATURE:
<223> OTHER INFORMATION: Synthetic primer

<400> SEQUENCE: 12
gccgcccgca ccgtccagcg gcttaag                                           27

<210> SEQ ID NO 13
<211> LENGTH: 33
<212> TYPE: DNA
<213> ORGANISM: Artificial Sequence
<220> FEATURE:
<223> OTHER INFORMATION: Synthetic primer

<400> SEQUENCE: 13
aagccgctgg acggtagcgg cggcgcgtcg att                                    33

<210> SEQ ID NO 14
<211> LENGTH: 33
<212> TYPE: DNA
<213> ORGANISM: Artificial Sequence
<220> FEATURE:
<223> OTHER INFORMATION: Synthetic primer

<400> SEQUENCE: 14
aatcgacgcg ccgccgctac cgtccagcgg ctt                                    33
```

<210> SEQ ID NO 15
<211> LENGTH: 33
<212> TYPE: DNA
<213> ORGANISM: Artificial Sequence
<220> FEATURE:
<223> OTHER INFORMATION: Synthetic primer

<400> SEQUENCE: 15
aagccgctgg acggtcatgg cggcgcgtcg att                               33

<210> SEQ ID NO 16
<211> LENGTH: 33
<212> TYPE: DNA
<213> ORGANISM: Artificial Sequence
<220> FEATURE:
<223> OTHER INFORMATION: Synthetic primer

<400> SEQUENCE: 16
aatcgacgcg ccgccatgac cgtccagcgg ctt                               33

<210> SEQ ID NO 17
<211> LENGTH: 33
<212> TYPE: DNA
<213> ORGANISM: Artificial Sequence
<220> FEATURE:
<223> OTHER INFORMATION: Synthetic primer

<400> SEQUENCE: 17
aagccgctgg acggtggcgg cggcgcgtcg att                               33

<210> SEQ ID NO 18
<211> LENGTH: 33
<212> TYPE: DNA
<213> ORGANISM: Artificial Sequence
<220> FEATURE:
<223> OTHER INFORMATION: Synthetic primer

<400> SEQUENCE: 18
aatcgacgcg ccgccgccac cgtccagcgg ctt                               33

<210> SEQ ID NO 19
<211> LENGTH: 35
<212> TYPE: DNA
<213> ORGANISM: Artificial Sequence
<220> FEATURE:
<223> OTHER INFORMATION: Synthetic primer

<400> SEQUENCE: 19
gtacccgggg atcctttact gctgctgtaa acgtg                             35

<210> SEQ ID NO 20
<211> LENGTH: 35
<212> TYPE: DNA
<213> ORGANISM: Artificial Sequence
<220> FEATURE:
<223> OTHER INFORMATION: Synthetic primer

<400> SEQUENCE: 20
gcctgcaggt cgactatgat caagctcggc atcgt                             35

<210> SEQ ID NO 21
<211> LENGTH: 1146
<212> TYPE: DNA
<213> ORGANISM: Kocuria rosea

<400> SEQUENCE: 21

```
gtggagatct cgttcgcccg ctcccaccag tcgacgctgg cgtcgagtg ggagatcgcc      60
ctcgtggacg gcaccaccgg ggatctcgtc cccgggggcc gggagacgtt cgaggccgtc     120
ctggacgccc accccgcctg ggcacggac ggcgaccacc cgcacctgac cggggagttc     180
ctgctcaaca ccgtcgagct ggtcaccggg gtgtgccggg acgtcgccca ctccaccgag     240
cagctgtcca ccatgctgga cgagatccgc aaggtcaccg acccgcaggg cctcgaggtc     300
ttcgccgccg gcacccaccc gttcgcccgc tggcaggacc agcaggtcac cgacaagcag     360
cgctaccaca agctcgtgga ccgcacccag tactggggcc ggcagatggt catctacggg     420
gtgcacgtgc acgtgggcct cgactcccgg gcgaaggcgc tgcccgtgct ggacgggctg     480
ctgacctact acccgcacct gctggcgctg tccgcgaact cgcccttctg gcgggcgag     540
gacaccggct atgcgtccca cgctccatg atcttccagc agctgtccac ggcggggctg     600
ccgtaccact cccgtcctg ggacgcgtac gagcagtgca tcacggacat gatcgccacc     660
ggcatcatcg aggagatgag cgaggcccgc tgggacgtgc cccgtgcc ccggctgggc     720
accgacgagg tgcgcttctg cgacgggctc tcgaccctgt gggaggtcgg ggcgctcacg     780
gcgctcaccc agtgcctcgc ggagtccatc tcccgggacg tggaggcggg ccggccccc     840
gcccgcctga agcctggca catccaggag aacaagtggc gcgccgcccg ctacggcctc     900
gacgccgagg tcatcaccga cccgcgcaac gtcgagcggg acctgcgcac ggacctgacc     960
gcgctgctcg accggctgga gcccgtggcc gcgcagctgg gctgctcccg cgagctcgcc    1020
gacgtggagc ggatcctgga gcagggcgcc ggctaccagc gccagcgcgc ggtcgcccgg    1080
gcccacgacg gggacctgca cgccgtcgcc ctcgacatcg tccgccgcac ccgggagaac    1140
gactga                                                               1146
```

<210> SEQ ID NO 22
<211> LENGTH: 381
<212> TYPE: PRT
<213> ORGANISM: Kocuria rosea

<400> SEQUENCE: 22

```
Met Glu Ile Ser Phe Ala Arg Ser His Gln Ser Thr Leu Gly Val Glu
 1               5                  10                  15

Trp Glu Ile Ala Leu Val Asp Gly Thr Thr Gly Asp Leu Val Pro Arg
            20                  25                  30

Gly Arg Glu Thr Phe Glu Ala Val Leu Asp Ala His Pro Ala Trp Gly
        35                  40                  45

Thr Asp Gly Asp His Pro His Leu Thr Gly Glu Phe Leu Leu Asn Thr
    50                  55                  60

Val Glu Leu Val Thr Gly Val Cys Arg Asp Val Ala His Ser Thr Glu
65                  70                  75                  80

Gln Leu Ser Thr Met Leu Asp Glu Ile Arg Lys Val Thr Asp Pro Gln
                85                  90                  95

Gly Leu Glu Val Phe Ala Ala Gly Thr His Pro Phe Ala Arg Trp Gln
           100                 105                 110

Asp Gln Gln Val Thr Asp Lys Gln Arg Tyr His Lys Leu Val Asp Arg
       115                 120                 125

Thr Gln Tyr Trp Gly Arg Gln Met Val Ile Tyr Gly Val His Val His
   130                 135                 140

Val Gly Leu Asp Ser Arg Ala Lys Ala Leu Pro Val Leu Asp Gly Leu
145                 150                 155                 160
```

Leu Thr Tyr Tyr Pro His Leu Leu Ala Leu Ser Ala Asn Ser Pro Phe
            165                 170                 175

Trp Ala Gly Glu Asp Thr Gly Tyr Ala Ser Gln Arg Ser Met Ile Phe
        180                 185                 190

Gln Gln Leu Ser Thr Ala Gly Leu Pro Tyr His Phe Pro Ser Trp Asp
    195                 200                 205

Ala Tyr Glu Gln Cys Ile Thr Asp Met Ile Ala Thr Gly Ile Ile Glu
210                 215                 220

Glu Met Ser Glu Ala Arg Trp Asp Val Arg Pro Val Pro Arg Leu Gly
225                 230                 235                 240

Thr Asp Glu Val Arg Phe Cys Asp Gly Leu Ser Thr Leu Trp Glu Val
                245                 250                 255

Gly Ala Leu Thr Ala Leu Thr Gln Cys Leu Ala Glu Ser Ile Ser Arg
            260                 265                 270

Asp Val Glu Ala Gly Arg Pro Pro Ala Arg Leu Lys Pro Trp His Ile
        275                 280                 285

Gln Glu Asn Lys Trp Arg Ala Arg Tyr Gly Leu Asp Ala Glu Val
    290                 295                 300

Ile Thr Asp Pro Arg Asn Val Glu Arg Asp Leu Arg Thr Asp Leu Thr
305                 310                 315                 320

Ala Leu Leu Asp Arg Leu Glu Pro Val Ala Ala Gln Leu Gly Cys Ser
                325                 330                 335

Arg Glu Leu Ala Asp Val Glu Arg Ile Leu Glu Gln Gly Ala Gly Tyr
            340                 345                 350

Gln Arg Gln Arg Ala Val Ala Arg Ala His Asp Gly Asp Leu His Ala
        355                 360                 365

Val Ala Leu Asp Ile Val Arg Arg Thr Arg Glu Asn Asp
    370                 375                 380

<210> SEQ ID NO 23
<211> LENGTH: 1182
<212> TYPE: DNA
<213> ORGANISM: Kocuria rhizophila

<400> SEQUENCE: 23

```
atgccgttcc cggcgcaccc acgagaggac cacgccgtgc acattgattt cgagacctcc      60
gagaactcca ccctgggtgt ggaatgggag gtcgcgctcg tggaccgcga atccggtgag     120
ctcgccccgc gcgcccagga ggtcctggag gccgtggtgg gcgagtaccc cgagctcggg     180
gaggagggcg accacccgca ggtcacgggc gagttcctgc agaacaccgt ggaaatggtc     240
acgggcgtgt gcagcgccgt tcccgaggcg gtggagcacc tcgcgcagac ccaggaccgg     300
atccggaaga tcaccgaccc ccgctccctg gaaatcttcg ccgcgggcac ccacccgttc     360
tcggactgga ccgagcagcc cgtggtggac gcggagcgct actacaaggt cctggaccgg     420
gcgcagtact ggggccggca gatggtgatc ttcggcatgc acgtgcacgt gggcatcgac     480
caccgggaca aggcgctgcc cgtgctcgac gggctcatga actactaccc ccacctgctg     540
gcgctgtccg cgaactcccc ctactggtgc ggccacgaca ccggctacgc ctcccaccgg     600
gcgctgatct tccagcagct ctccaccgcg ggctgccct tccacttcga ctcctggagc     660
gagtacgagg cctacgtctc ggacctcatg agaccggcg tgatcgagga gatctccgag     720
aaccgctggg acatccgccc cgtgccgcgc ttcggcaccg tggagatgcg cgtgtgcgac     780
gggccctcca acctccggga gatcggcgcc ctggccgcgc tgacgcagtg cctcgtggag     840
```

```
tccttctccc gcaccctgga cgaggggcgc agcattgcgg tgatgccccc gtggcaccac    900
caggagaaca gtggcgggc cgcccgctac gggctggacg ccgtggtgat ccggacgcc     960 cagaaccacg agcgccccgt ggcggaggac ctcaccgagg tgctcaaccg gctggagccc   1020
ctcgccgccg aactcggctg cgctgacgag ctgggctacg tggagaccat gatgacgggc   1080
gagaccggct accagcgcca gcggcggatc gcggaggcca acggcgggga cctgcgcgcc   1140
gtggtgcggg acatcgtggc gcagaaccgc gagatccgct ga                     1182
```

<210> SEQ ID NO 24
<211> LENGTH: 393
<212> TYPE: PRT
<213> ORGANISM: Kocuria rhizophila

<400> SEQUENCE: 24

```
Met Pro Phe Pro Ala His Pro Arg Glu Asp His Ala Val His Ile Asp
1               5                   10                  15

Phe Glu Thr Ser Glu Asn Ser Thr Leu Gly Val Glu Trp Glu Val Ala
            20                  25                  30

Leu Val Asp Arg Glu Ser Gly Glu Leu Ala Pro Arg Ala Gln Glu Val
        35                  40                  45

Leu Glu Ala Val Val Gly Glu Tyr Pro Glu Leu Gly Glu Gly Asp
    50                  55                  60

His Pro Gln Val Thr Gly Glu Phe Leu Gln Asn Thr Val Glu Met Val
65                  70                  75                  80

Thr Gly Val Cys Ser Ala Val Pro Glu Ala Val Glu His Leu Ala Gln
                85                  90                  95

Thr Gln Asp Arg Ile Arg Lys Ile Thr Asp Pro Arg Ser Leu Glu Ile
            100                 105                 110

Phe Ala Ala Gly Thr His Pro Phe Ser Asp Trp Thr Glu Gln Pro Val
        115                 120                 125

Val Asp Ala Glu Arg Tyr Tyr Lys Val Leu Asp Arg Ala Gln Tyr Trp
    130                 135                 140

Gly Arg Gln Met Val Ile Phe Gly Met His Val His Val Gly Ile Asp
145                 150                 155                 160

His Arg Asp Lys Ala Leu Pro Val Leu Asp Gly Leu Met Asn Tyr Tyr
                165                 170                 175

Pro His Leu Leu Ala Leu Ser Ala Asn Ser Pro Tyr Trp Cys Gly His
            180                 185                 190

Asp Thr Gly Tyr Ala Ser His Arg Ala Leu Ile Phe Gln Gln Leu Ser
        195                 200                 205

Thr Ala Gly Leu Pro Phe His Phe Asp Ser Trp Ser Glu Tyr Glu Ala
    210                 215                 220

Tyr Val Ser Asp Leu Met Glu Thr Gly Val Ile Glu Glu Ile Ser Glu
225                 230                 235                 240

Asn Arg Trp Asp Ile Arg Pro Val Pro Arg Phe Gly Thr Val Glu Met
                245                 250                 255

Arg Val Cys Asp Gly Pro Ser Asn Leu Arg Glu Ile Gly Ala Leu Ala
            260                 265                 270

Ala Leu Thr Gln Cys Leu Val Glu Ser Phe Ser Arg Thr Leu Asp Glu
        275                 280                 285

Gly Arg Ser Ile Ala Val Met Pro Pro Trp His Gln Glu Asn Lys
    290                 295                 300

Trp Arg Ala Ala Arg Tyr Gly Leu Asp Ala Val Val Ile Arg Asp Ala
305                 310                 315                 320
```

Gln Asn His Glu Arg Pro Val Ala Glu Asp Leu Thr Glu Val Leu Asn
            325                 330                 335

Arg Leu Glu Pro Leu Ala Ala Glu Leu Gly Cys Ala Asp Glu Leu Gly
        340                 345                 350

Tyr Val Glu Thr Met Met Thr Gly Glu Thr Gly Tyr Gln Arg Gln Arg
        355                 360                 365

Arg Ile Ala Glu Ala Asn Gly Gly Asp Leu Arg Ala Val Val Arg Asp
    370                 375                 380

Ile Val Ala Gln Asn Arg Glu Ile Arg
385                 390

<210> SEQ ID NO 25
<211> LENGTH: 1197
<212> TYPE: DNA
<213> ORGANISM: Micrococcus luteus

<400> SEQUENCE: 25
atgactctgc ccttcgccga ctccgcgcag tccactctcg aatcgagtg ggagctcgcg      60 ctcgtggacg ccgtgtccgg cgagctgcgc tccgaggccc agacctgct gcgcgccctg     120 catgtggccg agggcctggc cgacgacgac gtgaacccgc acatgaccag cgagctcctg     180
cagaacacgg tggagctcgt cacgggcgtg cacgagcgcg tcgacgccgc gacggcggac     240
ctcggccgga tcgccgcgcg cgtggccgac gccgcggcgg cgcggggcat ctccctgttc     300
tgccagggca cgcacccgtt cgcggacgcg atcgcgcagc cctcgacacc cagtgagcgc     360
tacgaccgca tgctggatct cacccagtac tggggtcggc agctgctgat cttcggcgtg     420
cacgtgcacg tgggcctgga cgacgtctcc aaggccatgc cggtggtgaa cggcctggtc     480
aaccgcgtgc cgcacctgct cgcactctcg gcctcctccc ccttctgggc gggcacggac     540
acgggctacc agtcccagcg caccctcctg ttccagcagc tgcccacggc cggcctgccg     600
ttccagttcc aggagtggga ggacttcgag cgctgcgtgg cccagatgga gcaggtgggc     660
atgatcgcgg acgtcaccga gtgccgctgg gacgtgcggg ccgtgccccg cctgggcacg     720
gtggagatgc gcgcgtgtga cggcctggcc acgtcgagg agatcgccgc cgtgaccgcc     780
tacacgcagt gcctcgtgga cgatctgtcc gcgagcctgg agcgcggtga cggtcgag     840 gtcctgccgc cgtggcacgc gcaggagaac aagtggcgcg ccgcccggta cggcatggac     900
gccaccgtga tcgtggacgc ccggggcacc caggttccgc tggcggagca cctgccggcg     960
gagatcgagc gactgacccc ggtcgccgag cggctgggct gcgaggcaga gctcgccggc    1020
gtccaggcga tgatcgacga cggcggcgcc gcgcgtcagc gtcgcgtgga ggcacaggcc    1080
ctggccggcc cgccggccga gggcgaggac gcggacgacg cggtggcccc gttgcgcgcg    1140
gtcgtgctgg acgccgccgc ccgcacccgc gcgtcgctgg acggccgcac cggctga     1197

<210> SEQ ID NO 26
<211> LENGTH: 398
<212> TYPE: PRT
<213> ORGANISM: Micrococcus luteus

<400> SEQUENCE: 26

Met Thr Leu Pro Phe Ala Asp Ser Ala Gln Ser Thr Leu Gly Ile Glu
1               5                   10                  15

Trp Glu Leu Ala Leu Val Asp Ala Val Ser Gly Glu Leu Arg Ser Glu
            20                  25                  30

Ala Pro Asp Leu Leu Arg Ala Leu His Val Ala Glu Gly Leu Ala Asp

```
             35                  40                  45
Asp Asp Val Asn Pro His Met Thr Ser Glu Leu Leu Gln Asn Thr Val
 50                  55                  60

Glu Leu Val Thr Gly Val His Glu Arg Val Asp Ala Ala Thr Ala Asp
 65                  70                  75                  80

Leu Gly Arg Ile Ala Ala Arg Val Ala Asp Ala Ala Ala Arg Gly
                 85                  90                  95

Ile Ser Leu Phe Cys Gln Gly Thr His Pro Phe Ala Asp Ala Ile Ala
                100                 105                 110

Gln Pro Ser Thr Pro Ser Glu Arg Tyr Asp Arg Met Leu Asp Leu Thr
            115                 120                 125

Gln Tyr Trp Gly Arg Gln Leu Leu Ile Phe Gly Val His Val His Val
        130                 135                 140

Gly Leu Asp Asp Val Ser Lys Ala Met Pro Val Val Asn Gly Leu Val
145                 150                 155                 160

Asn Arg Val Pro His Leu Leu Ala Leu Ser Ala Ser Ser Pro Phe Trp
                165                 170                 175

Ala Gly Thr Asp Thr Gly Tyr Gln Ser Gln Arg Thr Leu Leu Phe Gln
            180                 185                 190

Gln Leu Pro Thr Ala Gly Leu Pro Phe Gln Phe Gln Glu Trp Glu Asp
        195                 200                 205

Phe Glu Arg Cys Val Ala Gln Met Glu Gln Val Gly Met Ile Ala Asp
210                 215                 220

Val Thr Glu Cys Arg Trp Asp Val Arg Ala Val Pro Arg Leu Gly Thr
225                 230                 235                 240

Val Glu Met Arg Ala Cys Asp Gly Leu Ala Thr Leu Glu Glu Ile Ala
                245                 250                 255

Ala Val Thr Ala Tyr Thr Gln Cys Leu Val Asp Asp Leu Ser Ala Ser
            260                 265                 270

Leu Glu Arg Gly Glu Thr Val Glu Val Leu Pro Pro Trp His Ala Gln
        275                 280                 285

Glu Asn Lys Trp Arg Ala Ala Arg Tyr Gly Met Asp Ala Thr Val Ile
290                 295                 300

Val Asp Ala Arg Gly Thr Gln Val Pro Leu Ala Glu His Leu Pro Ala
305                 310                 315                 320

Glu Ile Glu Arg Leu Thr Pro Val Ala Glu Arg Leu Gly Cys Glu Ala
                325                 330                 335

Glu Leu Ala Gly Val Gln Ala Met Ile Asp Asp Gly Gly Ala Ala Arg
            340                 345                 350

Gln Arg Arg Val Glu Ala Gln Ala Leu Ala Gly Pro Pro Ala Glu Gly
        355                 360                 365

Glu Asp Ala Asp Asp Ala Ala Pro Leu Arg Ala Val Val Leu Asp
370                 375                 380

Ala Ala Ala Arg Thr Arg Ala Ser Leu Asp Gly Arg Thr Gly
385                 390                 395

<210> SEQ ID NO 27
<211> LENGTH: 1557
<212> TYPE: DNA
<213> ORGANISM: Escherichia coli

<400> SEQUENCE: 27
ttgatcccgg acgtatcaca ggcgctggcc tggctggaaa acatcctca ggcgttaaag      60 gggatacagc gtgggctgga gcgcgaaact ttgcgtgtta atgctgatgg cacactggca     120
```

```
acaacaggtc atcctgaagc attaggttcc gcactgacgc acaaatggat tactaccgat    180
tttgcggaag cattgctgga attcattaca ccagtggatg gtgatattga acatatgctg    240
acctttatgc gcgatctgca tcgttatacg gcgcgcaata tgggcgatga gcggatgtgg    300
ccgttaagta tgccatgcta catcgcagaa ggtcaggaca tcgaactggc acagtacggc    360
acttctaaca ccggacgctt taaaacgctg tatcgtgaag ggctgaaaaa tcgctacggc    420
gcgctgatgc aaaccatttc cggcgtgcac tacaatttct ctttgccaat ggcattctgg    480
caagcgaagt gcggtgatat ctcgggcgct gatgccaaag agaaaatttc tgcgggctat    540
ttccgcgtta ccgcaattac tatcgtttc ggttgggtca ttccttatct gtttggtgca    600
tctccggcga tttgttcttc tttcctgcaa ggaaaaccaa cgtcgctgcc gtttgagaaa    660
accgagtgcg gtatgtatta cctgccgtat gcgacctctc ttcgtttgag cgatctcggc    720
tataccaata atcgcaaag caatcttggt attaccttca acgatcttta cgagtacgta    780 gcgggccta aacaggcaat caaaacgcca tcggaagagt acgcgaagat tggtattgag    840
aaagacggta agaggctgca aatcaacagc aacgtgttgc agattgaaaa cgaactgtac    900
gcgccgattc gtccaaaacg cgttaccgcg agcggcgagt cgccttctga tgcgctgtta    960
cgtggcggca ttgaatatat tgaagtgcgt tcgctggaca tcaacccgtt ctcgccgatt   1020
ggtgtagatg aacagcaggt gcgattcctc gacctgttta tggtctggtg tgcgctggct   1080
gatgcaccgg aaatgagcag tagcgaactt gcctgtacac gcgttaactg gaaccgggtg   1140
atcctcgaag tcgcaaaacc gggtctgacg ctgggtatcg gctgcgaaac cgcacagttc   1200
ccgttaccgc aggtgggtaa agatctgttc cgcgatctga aacgcgtcgc gcaaacgctg   1260
gatagtatta acggcggcga agcgtatcag aaagtgtgtg atgaactggt tgcctgcttc   1320
gataatcccg atctgacttt ctctgcccgt atcttaaggt ctatgattga tactggtatt   1380
ggcggaacag gcaaagcatt tgcagaagcc taccgtaatc tgctgcgtga agagccgctg   1440
gaaattctgc gcgaagagga ttttgtagcc gagcgcgagg cgtctgaacg ccgtcagcag   1500
gaaatggaag ccgctgatac cgaaccgttt gcggtgtggc tggaaaaaca cgcctga     1557
```

<210> SEQ ID NO 28
<211> LENGTH: 518
<212> TYPE: PRT
<213> ORGANISM: Escherichia coli

<400> SEQUENCE: 28

Met Ile Pro Asp Val Ser Gln Ala Leu Ala Trp Leu Glu Lys His Pro
1               5                   10                  15

Gln Ala Leu Lys Gly Ile Gln Arg Gly Leu Glu Arg Glu Thr Leu Arg
            20                  25                  30

Val Asn Ala Asp Gly Thr Leu Ala Thr Thr Gly His Pro Glu Ala Leu
        35                  40                  45

Gly Ser Ala Leu Thr His Lys Trp Ile Thr Thr Asp Phe Ala Glu Ala
    50                  55                  60

Leu Leu Glu Phe Ile Thr Pro Val Asp Gly Asp Ile Glu His Met Leu
65                  70                  75                  80

Thr Phe Met Arg Asp Leu His Arg Tyr Thr Ala Arg Asn Met Gly Asp
                85                  90                  95

Glu Arg Met Trp Pro Leu Ser Met Pro Cys Tyr Ile Ala Glu Gly Gln
            100                 105                 110

Asp Ile Glu Leu Ala Gln Tyr Gly Thr Ser Asn Thr Gly Arg Phe Lys

```
            115                 120                 125
Thr Leu Tyr Arg Glu Gly Leu Lys Asn Arg Tyr Gly Ala Leu Met Gln
    130                 135                 140

Thr Ile Ser Gly Val His Tyr Asn Phe Ser Leu Pro Met Ala Phe Trp
145                 150                 155                 160

Gln Ala Lys Cys Gly Asp Ile Ser Gly Ala Asp Ala Lys Glu Lys Ile
                165                 170                 175

Ser Ala Gly Tyr Phe Arg Val Ile Arg Asn Tyr Tyr Arg Phe Gly Trp
            180                 185                 190

Val Ile Pro Tyr Leu Phe Gly Ala Ser Pro Ala Ile Cys Ser Ser Phe
        195                 200                 205

Leu Gln Gly Lys Pro Thr Ser Leu Pro Phe Glu Lys Thr Glu Cys Gly
    210                 215                 220

Met Tyr Tyr Leu Pro Tyr Ala Thr Ser Leu Arg Leu Ser Asp Leu Gly
225                 230                 235                 240

Tyr Thr Asn Lys Ser Gln Ser Asn Leu Gly Ile Thr Phe Asn Asp Leu
                245                 250                 255

Tyr Glu Tyr Val Ala Gly Leu Lys Gln Ala Ile Lys Thr Pro Ser Glu
            260                 265                 270

Glu Tyr Ala Lys Ile Gly Ile Glu Lys Asp Gly Lys Arg Leu Gln Ile
        275                 280                 285

Asn Ser Asn Val Leu Gln Ile Glu Asn Glu Leu Tyr Ala Pro Ile Arg
    290                 295                 300

Pro Lys Arg Val Thr Arg Ser Gly Glu Ser Pro Ser Asp Ala Leu Leu
305                 310                 315                 320

Arg Gly Gly Ile Glu Tyr Ile Glu Val Arg Ser Leu Asp Ile Asn Pro
                325                 330                 335

Phe Ser Pro Ile Gly Val Asp Glu Gln Gln Val Arg Phe Leu Asp Leu
            340                 345                 350

Phe Met Val Trp Cys Ala Leu Ala Asp Ala Pro Glu Met Ser Ser Ser
        355                 360                 365

Glu Leu Ala Cys Thr Arg Val Asn Trp Asn Arg Val Ile Leu Glu Gly
    370                 375                 380

Arg Lys Pro Gly Leu Thr Leu Gly Ile Gly Cys Glu Thr Ala Gln Phe
385                 390                 395                 400

Pro Leu Pro Gln Val Gly Lys Asp Leu Phe Arg Asp Leu Lys Arg Val
                405                 410                 415

Ala Gln Thr Leu Asp Ser Ile Asn Gly Gly Glu Ala Tyr Gln Lys Val
            420                 425                 430

Cys Asp Glu Leu Val Ala Cys Phe Asp Asn Pro Asp Leu Thr Phe Ser
        435                 440                 445

Ala Arg Ile Leu Arg Ser Met Ile Asp Thr Gly Ile Gly Gly Thr Gly
    450                 455                 460

Lys Ala Phe Ala Glu Ala Tyr Arg Asn Leu Leu Arg Glu Glu Pro Leu
465                 470                 475                 480

Glu Ile Leu Arg Glu Glu Asp Phe Val Ala Glu Arg Glu Ala Ser Glu
                485                 490                 495

Arg Arg Gln Gln Glu Met Glu Ala Ala Asp Thr Glu Pro Phe Ala Val
            500                 505                 510

Trp Leu Glu Lys His Ala
        515

<210> SEQ ID NO 29
```

<211> LENGTH: 1743
<212> TYPE: DNA
<213> ORGANISM: Escherichia coli

<400> SEQUENCE: 29

| | | |
|---|---|---|
| atgataaaac cgacgttttt acgccgggtg gccattgctg ctctgctctc aggaagttgt | 60 |
| tttagcgccg ccgccgcgcc tcctgcgccg cccgtctcgt atggtgtgga ggaagatgtc | 120 |
| ttccacccgg tacgcgcgaa acagggaatg gtagcgtctg tggacgccac tgccactcag | 180 |
| gtggggggtgg atattctcaa ggagggcggg aatgccgttg atgccgccgt ggcggtgggc | 240 |
| tacgcgctgg cggtaacgca tccgcaggca gggaatctgg cggtggtgg ttttatgtta | 300 |
| atccgctcga aaatggcaa taccacggct atcgatttcc gcgaaatggc acccgccaaa | 360 |
| gcgacccgcg atatgttcct cgatgatcag ggcaacccgg acagcaaaaa atcactcact | 420 |
| tcgcatctgg cttccggcac accgggtacg gtagcaggtt tctcgctggc gctggataaa | 480 |
| tacggcacca tgccgctgaa caaagtcgtg cagcccgcgt ttaaactggc acgcgatggt | 540 |
| tttatcgtta acgacgcgct ggctgacgat ctcaaaacct acggtagcga agtgttgccg | 600 |
| aatcacgaaa acagtaaagc tatcttctgg aaagagggcg agccgctgaa aaagggcgac | 660 |
| acgctggtgc aggcgaacct ggcaaagagc ctggagatga ttgctgaaaa cggcccggac | 720 |
| gaattctata aggcacgat tgcggaacag atcgcccagg agatgcagaa aaacggtggc | 780 |
| ttgatcacta agaagatttt agcagccat aaagcggtcg aacgcactcc gataagcggc | 840 |
| gattatcgcg ggtatcaggt ttactccatg ccaccgccat cctccggcgg gatccatatc | 900 |
| gtacaaatcc tcaatattct ggaaaacttc gatatgaaga atacggctt tggcagcgcc | 960 |
| gatgcgatgc aaatcatggc agaagcggag aaatacgcct acgccgaccg ctcggaatat | 1020 |
| cttggcgacc cggattttgt caaagtaccg tggcaggcgc tgaccaataa agcctatgcc | 1080 |
| aaatctattg ccgatcaaat tgatatcaat aaagcgaagc catccagcga aattcgcccc | 1140 |
| ggcaagcttg cgccttatga gagtaatcaa actacccatt actcagtggt ggataaagat | 1200 |
| ggtaacgcgg tggcggtgac ctatacgctg aacaccacct tcggtacggg cattgtcgcg | 1260 |
| ggcgagagcg gtattctgct taataaccag atggatgatt tctccgccaa ccgggcgta | 1320 |
| ccgaacgttt acgggctggt gggcggtgat gccaacgccg tcgggccgaa caaacgcccg | 1380 |
| ctgtcgtcga tgtcgccgac cattgtggtg aaagacggta aaacctggct ggttaccggt | 1440 |
| agcccaggcg gtagccggat catcactaca gtgctgcaaa tggtggtgaa tagcatcgat | 1500 |
| tatggcttga acgtcgccga agcgaccaat gcgccgcgtt tccaccatca gtggttgccg | 1560 |
| gacgagctgc gtgtcgaaaa agggtttagc ccggatacgc tcaagctgct ggaagcaaaa | 1620 |
| ggtcagaaag tggcgctgaa agaggcgatg ggcagtacac aaagcattat ggttgggccg | 1680 |
| gacggtgagt tgtacggcgc atccgacccg cgctcggtgg atgatttaac ggcggggtac | 1740 |
| taa | 1743 |

<210> SEQ ID NO 30
<211> LENGTH: 580
<212> TYPE: PRT
<213> ORGANISM: Escherichia coli

<400> SEQUENCE: 30

Met Ile Lys Pro Thr Phe Leu Arg Arg Val Ala Ile Ala Ala Leu Leu
1               5                   10                  15

Ser Gly Ser Cys Phe Ser Ala Ala Ala Ala Pro Pro Ala Pro Pro Val
            20                  25                  30

-continued

```
Ser Tyr Gly Val Glu Asp Val Phe His Pro Val Arg Ala Lys Gln
         35                  40                  45

Gly Met Val Ala Ser Val Asp Ala Thr Ala Thr Gln Val Gly Val Asp
 50                  55                  60

Ile Leu Lys Glu Gly Gly Asn Ala Val Asp Ala Ala Val Ala Val Gly
 65                  70                  75                  80

Tyr Ala Leu Ala Val Thr His Pro Gln Ala Gly Asn Leu Gly Gly Gly
                 85                  90                  95

Gly Phe Met Leu Ile Arg Ser Lys Asn Gly Asn Thr Ala Ile Asp
                100                 105                 110

Phe Arg Glu Met Ala Pro Ala Lys Ala Thr Arg Asp Met Phe Leu Asp
                115                 120                 125

Asp Gln Gly Asn Pro Asp Ser Lys Lys Ser Leu Thr Ser His Leu Ala
        130                 135                 140

Ser Gly Thr Pro Gly Thr Val Ala Gly Phe Ser Leu Ala Leu Asp Lys
145                 150                 155                 160

Tyr Gly Thr Met Pro Leu Asn Lys Val Val Gln Pro Ala Phe Lys Leu
                    165                 170                 175

Ala Arg Asp Gly Phe Ile Val Asn Asp Ala Leu Ala Asp Asp Leu Lys
                180                 185                 190

Thr Tyr Gly Ser Glu Val Leu Pro Asn His Glu Asn Ser Lys Ala Ile
        195                 200                 205

Phe Trp Lys Glu Gly Glu Pro Leu Lys Lys Gly Asp Thr Leu Val Gln
        210                 215                 220

Ala Asn Leu Ala Lys Ser Leu Glu Met Ile Ala Glu Asn Gly Pro Asp
225                 230                 235                 240

Glu Phe Tyr Lys Gly Thr Ile Ala Glu Gln Ile Ala Gln Glu Met Gln
                    245                 250                 255

Lys Asn Gly Gly Leu Ile Thr Lys Glu Asp Leu Ala Ala Tyr Lys Ala
                260                 265                 270

Val Glu Arg Thr Pro Ile Ser Gly Asp Tyr Arg Gly Tyr Gln Val Tyr
        275                 280                 285

Ser Met Pro Pro Pro Ser Ser Gly Gly Ile His Ile Val Gln Ile Leu
        290                 295                 300

Asn Ile Leu Glu Asn Phe Asp Met Lys Lys Tyr Gly Phe Gly Ser Ala
305                 310                 315                 320

Asp Ala Met Gln Ile Met Ala Glu Ala Glu Lys Tyr Ala Tyr Ala Asp
                    325                 330                 335

Arg Ser Glu Tyr Leu Gly Asp Pro Phe Val Lys Val Pro Trp Gln
                340                 345                 350

Ala Leu Thr Asn Lys Ala Tyr Ala Lys Ser Ile Ala Asp Gln Ile Asp
        355                 360                 365

Ile Asn Lys Ala Lys Pro Ser Ser Glu Ile Arg Pro Gly Lys Leu Ala
        370                 375                 380

Pro Tyr Glu Ser Asn Gln Thr Thr His Tyr Ser Val Val Asp Lys Asp
385                 390                 395                 400

Gly Asn Ala Val Ala Val Thr Tyr Thr Leu Asn Thr Thr Phe Gly Thr
                    405                 410                 415

Gly Ile Val Ala Gly Glu Ser Gly Ile Leu Leu Asn Asn Gln Met Asp
                420                 425                 430

Asp Phe Ser Ala Lys Pro Gly Val Pro Asn Val Tyr Gly Leu Val Gly
        435                 440                 445
```

```
Gly Asp Ala Asn Ala Val Gly Pro Asn Lys Arg Pro Leu Ser Ser Met
    450             455             460

Ser Pro Thr Ile Val Val Lys Asp Gly Lys Thr Trp Leu Val Thr Gly
465             470             475             480

Ser Pro Gly Gly Ser Arg Ile Ile Thr Thr Val Leu Gln Met Val Val
            485             490             495

Asn Ser Ile Asp Tyr Gly Leu Asn Val Ala Glu Ala Thr Asn Ala Pro
            500             505             510

Arg Phe His His Gln Trp Leu Pro Asp Glu Leu Arg Val Glu Lys Gly
        515             520             525

Phe Ser Pro Asp Thr Leu Lys Leu Leu Glu Ala Lys Gly Gln Lys Val
530             535             540

Ala Leu Lys Glu Ala Met Gly Ser Thr Gln Ser Ile Met Val Gly Pro
545             550             555             560

Asp Gly Glu Leu Tyr Gly Ala Ser Asp Pro Arg Ser Val Asp Asp Leu
            565             570             575

Thr Ala Gly Tyr
            580
```

MUTANT GLUTATHIONE SYNTHETASE AND METHOD FOR PRODUCING GAMMA-GLUTAMYL-VALYL-GLYCINE

TECHNICAL FIELD

The present invention relates to a mutant glutathione synthetase and a method for producing γ-glutamylvalylglycine using the same. γ-Glutamylvalylglycine is useful in the fields of food, drug, and so forth.

BACKGROUND ART

Certain kinds of peptides such as γ-glutamylvalylglycine (L-γ-glutamyl-L-valyl-glycine, henceforth also referred to as "γ-Glu-Val-Gly") have a calcium sensing receptor agonist activity (Patent document 1). Such peptides having a calcium receptor agonist activity are known to be able to impart "kokumi" to foods and drinks (Patent document 2), improve tastes of low fat foods, especially fat-like thickness and smoothness (Patent document 3), improve feeling of body of sweet taste substances, and improve bitterness peculiar to sweet taste substances (Patent document 4).

Moreover, such peptides as mentioned above are known to have a prophylactic or curative effect on diarrhea (Patent document 5) and diabetes (Patent document 6), and a bicarbonate secretion promoting effect in the alimentary tract (Patent document 7).

As methods for producing γ-glutamyl tripeptides, chemical synthesis methods and enzymatic methods are generally known. As one of the chemical synthesis methods, a method of selectively obtaining a γ-glutamyl tripeptide from a dipeptide by using N-protected glutamic anhydride is known (Patent document 8). As one of the enzymatic methods, there is known a method of using glutamate-cysteine ligase and glutathione synthetase is known (Patent documents 9 and 10). As another enzymatic method, there is also known a method of γ-glutamylating Val-Gly by using γ-glutamyl-transferase to generate γ-Glu-Val-Gly (Patent document 11).

As studies on biosynthesis of γ-glutamyl compounds, many studies on glutathione (γ-Glu-Cys-Gly; GSH) and a precursor thereof, γ-Glu-Cys, have been carried out. It is known that GSH is generated in vivo by generation of γ-Glu-Cys from Glu and Cys by glutamate-cysteine ligase and subsequent ligation of Gly by glutathione synthetase. It is known that glutamate-cysteine ligase is encoded by a GSH1 gene or a gshA gene and glutathione synthetase is encoded by a GSH2 gene or a gshB gene, and properties of these enzymes have been studied.

Glutathione synthetase (hereinafter also referred to as "GSHB") is known as an enzyme having an activity for catalyzing the reaction of generating γ-Glu-Cys-Gly, ADP, and phosphate by using γ-Glu-Cys, Gly, and ATP as the substrates (EC 6.3.2.3). GSHB generally requires divalent metal ions such as $Mg^{2+}$ and $Mn^{2+}$ for enzymatic reactions. GSHB may also catalyze synthesis of γ-glutamyl tripeptides other than GSH, such as γ-Glu-Val-Gly.

Regarding GSHB of *Escherichia coli*, it has been reported that a loop from Ile-226 to Arg-241 is an important structural unit for catalyzing the glutathione synthesis reaction (Non-patent document 1). This document discloses mutations R233A, R233K, R241A, and R241K. In addition, Non-patent document 2 discloses mutations P227A, P227V, G229A, G229V, G240A, G240V, and P227V/G240V. It has been also reported that cleavage or deletion of the loop from Ile-226 to Arg-241 results in a decrease in the glutathione synthesis activity (Non-patent document 3).

In addition, regarding GSHB of *Saccharomyces cerevisiae*, mutations and combinations thereof preferable for generation of γ-Glu-Val-Gly have been reported (Patent document 9).

However, regarding GSHB of *Escherichia coli*, no mutations or combinations thereof preferable for generation of γ-Glu-Val-Gly have been known.

PRIOR ART REFERENCES

Patent Documents

Patent document 1: WO2007/055388
Patent document 2: WO2007/055393
Patent document 3: WO2008/139945
Patent document 4: WO2008/139946
Patent document 5: WO2008/139947
Patent document 6: WO2009/107660
Patent document 7: WO2009/119554
Patent document 8: Japanese Patent Laid-open (Kokai) No. 08-119916
Patent document 9: WO2013/054447
Patent document 10: Japanese Patent Laid-open (Kokai) No. 2012-85637
Patent document 11: WO2013/051685

Non-Patent Documents

Non-patent document 1: Biochemistry, 31, 2259-2265 (1992)
Non-patent document 2: Biochemistry, 32, 12398-12404 (1993)
Non-patent document 3: Archives of biochemistry and biophysics, 339, 151-156 (1997)

SUMMARY OF THE INVENTION

Object to be Achieved by the Invention

An object of the present invention is to provide a mutant of GSHB suitable for generating γ-Glu-Val-Gly, and a method for producing γ-Glu-Val-Gly using the same.

Means for Achieving the Object

The inventors of the present invention conducted various researches in order to achieve the aforementioned object, as a result, found mutations of GSHB that improve the γ-Glu-Val-Gly synthesis activity, and accomplished the present invention.

Thus, the present invention can be embodied, for example, as follows.

[1] A mutant glutathione synthetase having a mutation at amino acid residue(s) corresponding to one or more amino acid residues selected from those mentioned below in a wild-type glutathione synthetase, and having the γ-glutamylvalylglycine synthetase activity:

V7, N13, I14, N15, K17, F22, F95, M165, N199, Y200, P202, I274, T285, P287.

[2] The mutant glutathione synthetase mentioned above, wherein the mutation includes a mutation corresponding to one or more mutations selected from those mentioned below:

V7(I), N13(K), I14(V), N15(H, K), K17(R, Y), F22(I), F95(L), M165(A, C, F, G, H, S, W), N199(A, E, G), Y200(F, H), P202(A), I274(M), T285(S), P287(V).

[3] The mutant glutathione synthetase mentioned above, wherein the mutation includes a mutation corresponding to any one of the following mutations:

M165H/V7I, M165H/N13K, M165H/I14V, M165H/N15K, M165H/N15H, M165H/K17Y, M165H/K17R, M165H/F22I, M165H/I274M, Y200F/M165S, Y200F/N199A, Y200F/N199G, Y200F/N199E, Y200F/P202A, Y200F/T285S, Y200F/F95L.

[4] The mutant glutathione synthetase mentioned above, wherein the wild-type glutathione synthetase is a protein defined in (a), (b), or (c) mentioned below:
(a) a protein comprising the amino acid sequence of SEQ ID NO: 2;
(b) a protein comprising the amino acid sequence of SEQ ID NO: 2 but including substitution, deletion, insertion, and/or addition of 1 to 10 amino acid residues;
(c) a protein comprising an amino acid sequence showing an identity of 90% or higher to the amino acid sequence of SEQ ID NO: 2.

[5] A method for producing γ-Glu-Val-Gly and/or a salt thereof, the method comprising the following step (B):
(B) a step of allowing the mutant glutathione synthetase mentioned above to act on γ-Glu-Val and Gly to generate γ-Glu-Val-Gly.

[6] The method mentioned above,
wherein the method further comprises the following step (A):
(A) a step of allowing γ-glutamylvaline synthetase to act on Glu and Val to generate γ-Glu-Val, and
wherein the γ-Glu-Val in the step (B) is the γ-Glu-Val generated in the step (A).

[7] A method for producing γ-Glu-Val-Gly and/or a salt thereof, the method comprising the following step (C):
(C) a step of allowing γ-glutamylvaline synthetase and the mutant glutathione synthetase mentioned above to act on Glu, Val, and Gly to generate γ-Glu-Val-Gly.

[8] The method mentioned above, wherein the mutant glutathione synthetase is a purified enzyme.

[9] The method mentioned above, wherein the mutant glutathione synthetase is an immobilized enzyme.

[10] The method mentioned above, wherein the mutant glutathione synthetase is an enzyme contained in a culture broth of a microorganism having the enzyme, cultured cells of the microorganism, or a processed product of the cells.

[11] The method mentioned above, wherein the γ-glutamylvaline synthetase is an enzyme contained in a culture broth of a microorganism having the enzyme, cultured cells of the microorganism, or a processed product of the cells.

[12] The method mentioned above, wherein the γ-glutamylvaline synthetase and the mutant glutathione synthetase are enzymes contained in a culture broth of a microorganism having both enzymes, cultured cells of the microorganism, or a processed product of the cells.

[13] A method for producing γ-Glu-Val-Gly and/or a salt thereof, the method comprising the following step (B):
(B) a step of culturing a microorganism having the mutant glutathione synthetase mentioned above in a culture medium to generate γ-Glu-Val-Gly from γ-Glu-Val and Gly.

[14] The method mentioned above,
wherein the method further comprises the following step (A):
(A) a step of culturing a microorganism having γ-glutamylvaline synthetase in a culture medium to generate γ-Glu-Val from Glu and Val, and
wherein the γ-Glu-Val in the step (B) is the γ-Glu-Val generated in the step (A).

[15] A method for producing γ-Glu-Val-Gly and/or a salt thereof, the method comprising the following step (C):
(C) a step of culturing a microorganism having γ-glutamylvaline synthetase and the mutant glutathione synthetase mentioned above in a culture medium to generate γ-Glu-Val-Gly from Glu, Val, and Gly.

[16] The method mentioned above, wherein the microorganism has been modified so that the activity of γ-glutamyltransferase is reduced as compared with a non-modified strain.

[17] The method mentioned above, wherein the microorganism is *Escherichia coli*.

[18] The method mentioned above, wherein the step or steps is/are carried out in the presence of ATP.

[19] The method mentioned above, wherein the γ-glutamylvaline synthetase is a protein defined in (a), (b), or (c) mentioned below:
(a) a protein comprising the amino acid sequence of SEQ ID NO: 22, 24, or 26;
(b) a protein comprising the amino acid sequence of SEQ ID NO: 22, 24, or 26 but including substitution, deletion, insertion, and/or addition of 1 to 10 amino acid residues, and having the γ-glutamylvaline synthetase activity;
(c) a protein comprising an amino acid sequence showing an identity of 90% or higher to the amino acid sequence of SEQ ID NO: 22, 24, or 26, and having the γ-glutamylvaline synthetase activity.

[20] The method mentioned above, wherein the γ-glutamylvaline synthetase is a mutant glutamate-cysteine ligase having a mutation at amino acid residue(s) corresponding to one or more amino acid residues selected from those mentioned below in a wild-type glutamate-cysteine ligase, and having the γ-glutamylvaline synthetase activity:

L135, Q144, Y241, N243, Y300.

[21] The method mentioned above, wherein the wild-type glutamate-cysteine ligase is a protein defined in (a), (b), or (c) mentioned below:
(a) a protein comprising the amino acid sequence of SEQ ID NO: 28;
(b) a protein comprising the amino acid sequence of SEQ ID NO: 28 but including substitution, deletion, insertion, and/or addition of 1 to 10 amino acid residues;
(c) a protein comprising an amino acid sequence showing an identity of 90% or higher to the amino acid sequence of SEQ ID NO: 28.

[22] A gene encoding the mutant glutathione synthetase mentioned above.

[23] A vector carrying the gene mentioned above.

[24] A microorganism having the gene mentioned above.

[25] The microorganism mentioned above, which has been modified so that the activity of γ-glutamyltransferase is reduced as compared with a non-modified strain.

[26] The microorganism mentioned above, which has a gene encoding γ-glutamylvaline synthetase.

[27] The microorganism mentioned above, which is *Escherichia coli*.

BRIEF DESCRIPTION OF THE DRAWING

The drawing is a diagram showing results of γ-Glu-Val-Gly production using mutant GSHB-expressing strains.

MODES FOR CARRYING OUT THE INVENTION

Hereafter, the present invention will be explained in detail. In this description, amino acids are L-amino acids, unless especially indicated.

<1> Mutant Glutathione Synthetase (Mutant GSHB)

Glutathione synthetase is generally known as an enzyme having an activity for catalyzing a reaction of generating glutathione (γ-Glu-Cys-Gly), ADP, and phosphate by using γ-Glu-Cys, Gly, and ATP as the substrates (EC 6.3.2.3). In the present invention, this activity is also referred to as "glutathione synthetase activity" or "glutathione synthesis activity". In the present invention, glutathione synthetase is also referred to as "GSHB". In the present invention, a gene encoding a GSHB is also referred to as "GSHB gene".

Furthermore, in the present invention, an activity for catalyzing a reaction of generating γ-Glu-Val-Gly, ADP, and phosphate using γ-Glu-Val, Gly, and ATP as substrates is also referred to as "γ-glutamylvalylglycine synthetase activity" or "γ-Glu-Val-Gly synthesis activity".

These enzymatic activities each can be measured on the basis of, for example, generation of the corresponding γ-glutamyl tripeptide upon allowing an enzyme to act on the substrates under appropriate conditions. These enzymatic activities each can be measured, for example, in the presence of a divalent metal ion. Examples of the divalent metal ion include $Mg^{2+}$ and $Mn^{2+}$.

The γ-glutamylvalylglycine synthetase activity can be measured by, for example, using an appropriate amount (e.g. 0.025 mg/mL in terms of a purified enzyme) of an enzyme with a reaction mixture composition of 10 mM γ-Glu-Val, 10 mM Gly, 10 mM ATP, 10 mM $MgSO_4$, 100 mM Tris-HCl buffer (pH 9.0) at a reaction temperature of 30° C. for a reaction time of from 1 minute to 50 hours (e.g. 30 minutes). The enzymatic activity for generating 1 μmol of γ-Glu-Val-Gly in 1 minute under the aforementioned conditions is defined as 1 U of the γ-glutamylvalylglycine synthetase activity.

In the present invention, the term "mutant glutathione synthetase (mutant GSHB)" refers to a GSHB having a "specific mutation". In the present invention, a gene encoding a mutant GSHB is also referred to as "mutant glutathione synthetase gene (mutant GSHB gene)". The "specific mutation" will be described later.

In the present invention, a GSHB not having the "specific mutation" is also referred to as "wild-type glutathione synthetase (wild-type GSHB)". In the present invention, a gene encoding a wild-type GSHB is also referred to as "wild-type glutathione synthetase gene (wild-type GSHB gene)". The term "wild-type" is used for convenience for distinguishing the "wild-type" ones from the "mutant" ones, and the wild-type gene or enzyme is not limited to a naturally occurring one, so long as the gene or enzyme does not have the "specific mutation".

Hereafter, the wild-type GSHB will be explained.

Examples of the wild-type GSHB include the GshB protein encoded by the gshB gene of *Escherichia coli*. The nucleotide sequence of the gshB gene of the *Escherichia coli* K-12 MG1655 strain is disclosed in Blattner FR, et al., Science, 277:1453-62 (1997), and corresponds to the sequence of positions 3,089,900 to 3,090,850 in the genome sequence registered at the NCBI database as GenBank accession NC_000913.3. The nucleotide sequence of the gshB gene of the *Escherichia coli* K-12 W3110 strain is the same as that of the MG1655 strain. The nucleotide sequence of the gshB gene of the W3110 strain is shown as SEQ ID NO: 1. The amino acid sequence of the protein encoded by this gene is shown as SEQ ID NO: 2. That is, the wild-type GSHB may be, for example, a protein encoded by a gene having the nucleotide sequence shown as SEQ ID NO: 1. The wild-type GSHB may also be, for example, a protein having the amino acid sequence shown as SEQ ID NO: 2. The expression "a gene or protein has a nucleotide or amino acid sequence" means that a gene or protein comprises the nucleotide or amino acid sequence unless otherwise stated, and also includes cases where a gene or protein consists of the nucleotide or amino acid sequence.

The wild-type GSHB may be a variant of the wild-type GSHB exemplified above (for example, a protein having the amino acid sequence shown as SEQ ID NO: 2), so long as it does not have the "specific mutation". That is, the wild-type GSHB may have another mutation, so long as it does not have the "specific mutation". Examples of the variant include, for example, a homologue of the wild-type GSHB exemplified above and an artificially modified version of the wild-type GSHB exemplified above. Examples of the homologue of GSHB of *Escherichia coli* include GSHB homologues of other microorganisms, of which structure is similar to that of GSHB of *Escherichia coli*. Examples of the GSHB homologues of other microorganisms include GSHB homologues of bacteria belonging to the family Enterobacteriaceae such as other *Escherichia* bacteria, *Enterobacter* bacteria, and *Pantoea* bacteria. GSHB homologues of other microorganisms can be obtained from, for example, a public database by BLAST search and FASTA search using the amino acid sequence of the wild-type GSHB exemplified above as a query sequence.

The wild-type GSHB may typically be a protein having the glutathione synthetase activity. However, in the present invention, so long as the corresponding mutant GSHB has the γ-glutamylvalylglycine synthetase activity, the wild-type GSHB may have the glutathione synthetase activity, the γ-glutamylvalylglycine synthetase activity, or a combination of these activities, or may have none of these activities.

The wild-type GSHB may be a protein having an amino acid sequence corresponding to the amino acid sequence of the wild-type GSHB exemplified above (for example, the amino acid sequence shown in SEQ ID NO: 2), but including substitution, deletion, insertion, and/or addition of one or several amino acid residues at one or several positions, so long as it does not have the "specific mutation". Although the number meant by the term "one or several" can differ depending on the positions of amino acid residues in the three-dimensional structure of the protein, or the types of amino acid residues, specifically, for example, it is 1 to 50, 1 to 40, 1 to 30, preferably 1 to 20, more preferably 1 to 10, still more preferably 1 to 5, particularly preferably 1 to 3.

The aforementioned substitution, deletion, insertion, or addition of one or several amino acid residues may be a conservative mutation that maintains normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, or addition of amino acid residues as mentioned above includes a naturally occurring mutation (mutant or variant), such as those due to a difference of individuals or species of the organism from which the gene is derived.

The wild-type GSHB may be a protein having an amino acid sequence showing a homology of 80% or higher, preferably 90% or higher, more preferably 95% or higher, still more preferably 97% or higher, particularly preferably 99% or higher, to the amino acid sequence of the wild-type GSHB exemplified above (for example, the amino acid sequence shown in SEQ ID NO: 2), so long as it does not have the "specific mutation". In this description, "homology" means "identity".

The wild-type GSHB may be a protein encoded by a DNA, such as a gene, that is able to hybridize under stringent conditions with a probe that can be prepared from the nucleotide sequence of the wild-type GSHB gene exemplified above (for example, the nucleotide sequence shown in SEQ ID NO: 1), such as a probe having a sequence complementary to a part or the whole of the nucleotide sequence of the wild-type GSHB gene exemplified above (for example, the nucleotide sequence shown in SEQ ID NO: 1), so long as it does not have the "specific mutation". Such a probe can be prepared by PCR using oligonucleotides produced on the basis of a known wild-type GSHB gene sequence as primers, and a DNA fragment containing the nucleotide sequence of the wild-type GSHB gene as the template. The "stringent conditions" refer to conditions under which a so-called specific hybrid is formed, and a non-specific hybrid is not formed. Examples of the stringent conditions include those under which highly homologous DNAs hybridize to each other, for example, DNAs not less than 80% homologous, preferably not less than 90% homologous, more preferably not less than 95% homologous, still more preferably not less than 97% homologous, particularly preferably not less than 99% homologous, hybridize to each other, and DNAs less homologous than the above do not hybridize to each other, or conditions of washing of typical Southern hybridization, i.e., conditions of washing once, preferably 2 or 3 times, at a salt concentration and temperature corresponding to 1×SSC, 0.1% SDS at 60° C., preferably 0.1×SSC, 0.1% SDS at 60° C., more preferably 0.1×SSC, 0.1% SDS at 68° C. Furthermore, for example, when a DNA fragment having a length of about 300 bp is used as the probe, the washing conditions of the hybridization can be, for example, 50° C., 2×SSC, and 0.1% SDS. Those skilled in the art can realize stringency equivalent to the stringency of the hybridization exemplified above by determining various conditions such as salt concentrations and temperature.

Furthermore, in the wild-type GSHB gene, any codons may be replaced with equivalent codons, so long as it encodes a wild-type GSHB. That is, the wild-type GSHB gene may be a variant of the wild-type GSHB gene exemplified above due to the degeneracy of the genetic code. For example, in the wild-type GSHB gene, codons may be optimized according to codon frequencies observed in the host to be used. Specifically, for example, when the start codon is not ATG, the start codon can be modified to ATG.

The percentage of the sequence identity between two sequences can be determined by, for example, using a mathematical algorithm. Non-limiting examples of such a mathematical algorithm include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and an modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison (i.e. alignment) for determining the sequence identity can be performed. The program can be appropriately executed by a computer. Examples of such a program include, but not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244 (1988), Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See www(dot)ncbi(dot)nlm(dot)nih(dot)gov for BLAST nucleotide search and BLAST protein search. In addition, Gapped BLAST (BLAST 2.0) can be used in order to obtain an alignment including gap(s) for the purpose of comparison. In addition, PSI-BLAST (BLAST 2.0) can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other. The term "identity" between amino acid sequences may specifically mean an identity calculated by blastp with default scoring parameters (i.e. Matrix, BLOSUM62; Gap Costs, Existence=11, Extension=1; Compositional Adjustments, Conditional compositional score matrix adjustment), unless otherwise stated. The term "identity" between nucleotide sequences may specifically mean an identity calculated by blastn with default scoring parameters (i.e. Match/Mismatch Scores=1, −2; Gap Costs=Linear), unless otherwise stated.

The aforementioned descriptions concerning variants of genes and proteins can be applied *mutatis mutandis* to variants of any proteins, such as GSHA and GGT, and genes encoding them.

Hereafter, the mutant GSHB will be explained.

The mutant GSHB has the γ-glutamylvalylglycine synthetase activity.

So long as the mutant GSHB has the γ-glutamylvalylglycine synthetase activity, it may or may not have an activity for generating a γ-glutamyl tripeptide other than γ-glutamylvalylglycine. That is, for example, the mutant GSHB may or may not have the glutathione synthetase activity.

The mutant GSHB has the "specific mutation" in the amino acid sequence of the wild-type GSHB.

That is, for example, the mutant GSHB may be a protein having the amino acid sequence shown as SEQ ID NO: 2, but including the "specific mutation". The mutant GSHB may also be, for example, a protein having the amino acid sequence shown as SEQ ID NO: 2, but including the "specific mutation", further including substitution, deletion, insertion, and/or addition of one or several amino acid residues at a site other than that of the "specific mutation", and having the γ-glutamylvalylglycine synthetase activity.

In other words, the mutant GSHB may be a protein having an amino acid sequence identical to that of the wild-type GSHB, except that it has the "specific mutation". For example, the mutant GSHB may be a protein having the amino acid sequence shown as SEQ ID NO: 2, except that it has the "specific mutation". The mutant GSHB may also be, for example, a protein having the amino acid sequence shown as SEQ ID NO: 2, but including substitution, deletion, insertion, and/or addition of one or several amino acid residues, and having the γ-glutamylvalylglycine synthetase activity, except that it has the "specific mutation". The mutant GSHB may also be, for example, a protein having an amino acid sequence showing a homology of 80% or higher, preferably 90% or higher, more preferably 95% or higher, still more preferably 97% or higher, particularly preferably 99% or higher, to the amino acid sequence shown as SEQ ID NO: 2, and having the γ-glutamylvalylglycine synthetase activity, except that it has the "specific mutation".

The mutant GSHB may have another amino acid sequence in addition to such an amino acid sequence of the mutant GSHB as exemplified above. That is, the mutant GSHB may be a fusion protein with another amino acid sequence. The same shall apply to the wild-type GSHB. The "another amino acid sequence" is not particularly limited, so long as the mutant GSHB has the γ-glutamylvalylglycine synthetase activity. The "another amino acid sequence" can be appropriately selected depending on various conditions such as use purpose thereof. Examples of the "another amino acid sequence" include, for example, a peptide tag, a signal peptide (also referred to as "signal sequence"), and a recognition sequence of a protease. The "another amino acid sequence" may be bound to, for example, either one or both of the N-terminus and C-terminus of the mutant GSHB. As the "another amino acid sequence", one kind of amino acid sequence may be used, or two or more kinds of amino acid sequences may be used in combination.

Specific examples of the peptide tag include an His tag, FLAG tag, GST tag, Myc tag, MBP (maltose binding protein), CBP (cellulose binding protein), TRX (thioredoxin), GFP (green fluorescent protein), HRP (horseradish peroxidase), ALP (alkaline phosphatase), and Fc region of antibody. Examples of the His tag include 6xHis tag. A peptide tag can be utilized for, for example, detection and purification of the expressed mutant GSHB.

The signal peptide is not particularly limited, so long as it functions in a host in which the mutant GSHB is expressed. Examples of the signal peptide include a signal peptide that is recognized by the Sec system secretory pathway and a signal peptide recognized by the Tat system secretory pathway. Specific examples of the signal peptide that is recognized by the Tat system secretory pathway include the TorA signal sequence of *E. coli*, the SufI signal sequence of *E. coli*, the PhoD signal sequence of *Bacillus subtilis*, the LipA signal sequence of *Bacillus subtilis*, and the IMD signal sequence of *Arthrobacter globiformis* (WO2013/118544). A signal peptide can be used for, for example, secretory production of the mutant GSHB. If secretory production of the mutant GSHB is performed by using a signal peptide, the signal peptide may be cleaved at the time of the secretion, and the mutant GSHB not having the signal peptide may be secreted out of the cell. That is, the phrase "a mutant GSHB comprises a signal peptide" means that it is sufficient that the mutant GSHB constitutes a fusion protein with a signal peptide at the time of expression, and it does not necessarily mean that the eventually-obtained mutant GSHB constitutes a fusion protein with a signal peptide.

Specific examples of the recognition sequence of a protease include the recognition sequence of the Factor Xa protease and the recognition sequence of the proTEV protease. The recognition sequence of a protease can be used for, for example, cleavage of the expressed mutant GSHB. Specifically, for example, when the mutant GSHB is expressed as a fusion protein with a peptide tag, if a recognition sequence of a protease is introduced into the connection part of the mutant GSHB and the peptide tag, the peptide tag can be cleaved from the expressed mutant GSHB by using a protease to obtain the mutant GSHB not having the peptide tag.

The mutant GSHB gene is not particularly limited so long as it encodes such a mutant GSHB as mentioned above. In the present invention, a "gene" is not limited to DNA, but may include any polynucleotide, so long as it encodes a target protein. That is, the "mutant GSHB gene" may mean any polynucleotide encoding a mutant GSHB. The mutant GSHB gene may be DNA, RNA, or a combination thereof. The mutant GSHB gene may be single-stranded or double-stranded. The mutant GSHB gene may be a single-stranded DNA or a single-stranded RNA. The mutant GSHB gene may be a double-stranded DNA, a double-stranded RNA, or a hybrid strand consisting of a DNA strand and an RNA strand. The mutant GSHB gene may contain both a DNA residue and an RNA residue in a single polynucleotide chain. When the mutant GSHB gene contains RNA, the aforementioned descriptions concerning DNA, such as those concerning nucleotide sequences exemplified above, may be applied to RNA with appropriately changing wordings to those for RNA as required. The mode of the mutant GSHB gene can be chosen according to various conditions such as use thereof.

Hereafter, the "specific mutation" will be explained.

The "specific mutation" refers to a mutation that imparts a characteristic suitable for generation of γ-glutamylvalylglycine to the wild-type GSHB, when it is introduced into the wild-type GSHB. That is, because of having the "specific mutation", the mutant GSHB has a characteristic suitable for generation of γ-glutamylvalylglycine, compared with the wild-type GSHB. Examples of the characteristic suitable for generation of γ-glutamylvalylglycine include, for example, an increase in the γ-glutamylvalylglycine synthetase activity (specifically, the specific activity). The γ-glutamylvalylglycine synthetase activity (specifically, the specific activity) of the mutant GSHB, for example, may be 1.1 times or more, 1.5 times or more, 2 times or more, 3 times or more, 5 times or more, 7 times or more, 10 times or more, or 20 times or more of that of the wild-type GSHB, may be 10,000,000 times or less, 1,000,000 times or less, 100,000 times or less, 10,000 times or less, 1,000 times or less, 100 times or less, 50 times or less, 20 times or less, 15 times or less, 10 times or less, 7 times or less, 5 times or less, 3 times or less, or 2 times or less of that of the wild-type GSHB, or may be within a range defined by any non-contradictory combination of the aforementioned ranges. The γ-glutamylvalylglycine synthetase activity (specifically, the specific activity) of the mutant GSHB may specifically be, for example, 1.1 to 2 times, 2 to 3 times, 3 to 5 times, 5 to 7 times, 7 to 10 times, 10 to 15 times, 1.1 to 3 times, 3 to 7 times, 7 to 15 times, 1.1 to 7 times, or 3 to 15 times of that of the wild-type GSHB. Specific examples of mutations providing these ranges of activity ratio include mutations showing relative γ-Glu-Val-Gly synthesis activities falling within these ranges of activity ratio in Table 3 of Examples section.

Examples of the "specific mutation" include a mutation corresponding to a mutation at one or more amino acid residues selected from the followings:

V7, N13, I14, N15, K17, F22, F95, M165, N199, Y200, P202, I274, T285, P287.

In the aforementioned description, the numerals indicate the positions in the amino acid sequence of the wild-type GSHB shown as SEQ ID NO: 2, and the letters on the left side of the numerals indicate the amino acid residues at the respective positions in the amino acid sequence of the wild-type GSHB shown as SEQ ID NO: 2 (namely, the amino acid residues before being mutated, indicated with one-letter code). For example, "M165" indicates the Met residue at position 165 in the amino acid sequence of the wild-type GSHB shown as SEQ ID NO: 2.

As for the aforementioned mutation, the amino acid residues after substitution may be any amino acid residues other than the original amino acid residues, so long as the mutant GSHB has the γ-glutamylvalylglycine synthetase activity. Specific examples of the amino acid residue after the substitution include K (Lys), R (Arg), H (His), A (Ala), V (Val), L (Leu), I (Ile), G (Gly), S (Ser), T (Thr), P (Pro), F (Phe), W (Trp), Y (Tyr), C (Cys), M (Met), D (Asp), E (Glu), N (Asn), and Q (Gln), which should be other than the original amino acid residues.

Specific examples of the "specific mutation" include a mutation corresponding to one or more mutations selected from the followings. That is, the "specific mutation" may include a mutation corresponding to one or more mutations selected from the followings. The "specific mutation" may be, for example, a mutation corresponding to any one of mutation selected from the followings, or may be a mutation corresponding to a combination of two or more mutations selected from the followings.

V7(I), N13(K), I14(V), N15(H, K), K17(R, Y), F22(I), F95(L), M165(A, C, F, G, H, S, W), N199(A, E, G), Y200(F, H), P202(A), I274(M), T285(S), P287(V).

In the aforementioned descriptions, the meanings of the numerals and the letters on the left side of the numerals are the same as those described above. The letters in the parentheses on the right side of the numerals indicate the amino acid residues (one-letter code) after being mutated. Namely, for example, "M165(A, C, F, G, H, S, W)" means a mutation that the Met residue at position 165 in the amino acid sequence of the wild-type GSHB shown as SEQ ID NO: 2 is replaced with any one of amino acid residues of Ala, Cys, Phe, Gly, His, Ser, and Trp. The amino acid residues after being mutated may also be mentioned without parenthesis. That is, for example, "M165H" means a mutation that the Met residue at position 165 in the amino acid sequence of the wild-type GSHB shown as SEQ ID NO: 2 is replaced with a His residue.

Combination of the mutations is not particularly limited. Examples of combination of the mutations include combinations comprising a mutation corresponding to a mutation at either one or both of M165 and Y200. Specific examples of combination of the mutations include combinations comprising a mutation corresponding to either one or both of M165(A, C, F, G, H, S, W) and Y200(F, H). More specific examples of combination of the mutations include double mutations comprising a mutation corresponding to a mutation at M165 such as M165(A, C, F, G, H, S, W), and double mutations comprising a mutation corresponding to a mutation at Y200 such as Y200(F, H). Further specific examples of combination of the mutations include the following combinations:

M165H/V7I, M165H/N13K, M165H/I14V, M165H/N15K, M165H/N15H, M165H/K17Y, M165H/K17R, M165H/F22I, M165H/I274M, Y200F/M165S, Y200F/N199A, Y200F/N199G, Y200F/N199E, Y200F/P202A, Y200F/T285S, Y200F/F95L.

In the aforementioned descriptions, the meanings of the numerals and the letters on the left and right sides of the numerals are the same as those described above. In the aforementioned descriptions, two or more mutations separated with "/" indicate a double or more multiple mutation. That is, for example, "M165H/V7I" indicates a double mutation of M165H and V7I.

A "mutation corresponding to a mutation of an amino acid residue at position n in the amino acid sequence shown as SEQ ID NO: 2" in the amino acid sequence of any chosen wild-type GSHB means a mutation at an amino acid residue corresponding to the amino acid residue at position n in the amino acid sequence shown as SEQ ID NO: 2. That is, for example, a "mutation corresponding to M165H" indicates a mutation that an amino acid residue corresponding to the Met residue at position 165 (M165) in the amino acid sequence of wild-type GSHB shown as SEQ ID NO: 2 is replaced with a His residue. The "amino acid residue corresponding to M165" mentioned here may typically be a Met residue, but may not be a Met residue. Namely, for example, the "mutation corresponding to M165H" is not limited to a mutation that when the "amino acid residue corresponding to M165" is a Met residue, the Met residue is replaced with a His residue, but includes a mutation that when the "amino acid residue corresponding to M165" is Lys, Arg, Ala, Val, Leu, Ile, Gly, Ser, Thr, Pro, Phe, Trp, Tyr, Cys, Asp, Glu, Asn, or Gln residue, this amino acid residue is replaced with a His residue. The same shall apply to the other mutations.

An "amino acid residue corresponding to the amino acid residue at position n in the amino acid sequence shown as SEQ ID NO: 2" in the amino acid sequence of any chosen wild-type GSHB means an amino acid residue corresponding to the amino acid residue at position n in the amino acid sequence shown as SEQ ID NO: 2 in an alignment of the target amino acid sequence of wild-type GSHB and the amino acid sequence of SEQ ID NO: 2. That is, as for the aforementioned mutation, the position of an amino acid residue does not necessarily indicate an absolute position in the amino acid sequence of a wild-type GSHB, but indicates a relative position based on the amino acid sequence shown as SEQ ID NO: 2. For example, when one amino acid residue is deleted at a position on the N-terminus side of position n in the wild-type GSHB consisting of the amino acid sequence shown as SEQ ID NO: 2, the amino acid residue originally at position n becomes an (n−1)th amino acid residue counted from the N-terminus, but it is regarded as the "amino acid residue corresponding to the amino acid residue at position n in the amino acid sequence shown as SEQ ID NO: 2". Similarly, for example, when an amino acid residue at position 100 in the amino acid sequence of a GSHB homologue of a certain microorganism corresponds to position 101 of the amino acid sequence shown as SEQ ID NO: 2, this amino acid residue is the "amino acid residue corresponding to the amino acid residue at position 101 in the amino acid sequence shown as SEQ ID NO: 2" in the GSHB homologue.

Such alignment can be performed by, for example, using known gene analysis software. Specific examples of such software include DNASIS produced by Hitachi Solutions, GENETYX produced by Genetyx, ClustalW opened to the public by DDBJ, and so forth (Elizabeth C. Tyler et al., Computers and Biomedical Research, 24(1), 72-96, 1991; Barton G. J. et al., Journal of Molecular Biology, 198 (2), 327-37, 1987; Thompson JD et al., Nucleic Acid Research, 22 (22), 4673-80, 1994).

<2> Production of Mutant Glutathione Synthetase (Mutant GSHB)

The mutant GSHB can be produced by making a host having the mutant GSHB gene express the mutant GSHB gene. The host having the mutant GSHB gene can be obtained by introducing the mutant GSHB gene into an appropriate host. The phrase "introducing a mutant GSHB gene into a host" also includes modifying the GSHB gene on the chromosome of the host so as to have the "specific mutation". A host having a mutant GSHB gene is also referred to as "host having a mutant GSHB". The mutant GSHB can also be produced by expressing the mutant GSHB gene in a cell-free protein synthesis system.

The mutant GSHB gene can be obtained by, for example, modifying the wild-type GSHB gene so that the encoded protein has the aforementioned "specific mutation". The original wild-type GSHB gene to be modified can be obtained by, for example, cloning from an organism having the wild-type GSHB gene, or chemical synthesis. The mutant GSHB gene can also be obtained without using the wild-type GSHB gene. For example, the mutant GSHB gene may be directly obtained by chemical synthesis etc. The obtained mutant GSHB gene may be further modified before use. For example, a mutant GSHB gene may be further modified to obtain another mutant GSHB gene.

Modification of a gene can be performed by a known method. For example, by the site-specific mutagenesis method, an objective mutation can be introduced into a target site of DNA. Examples of the site-specific mutagenesis method include a method using PCR (Higuchi, R., 61, in PCR Technology, Erlich, H. A. Eds., Stockton Press, 1989; Carter P., Meth., in Enzymol., 154, 382, 1987), and a method of using a phage (Kramer, W. and Frits, H. J., Meth. in Enzymol., 154, 350, 1987; Kunkel, T. A. et al., Meth. in Enzymol., 154, 367, 1987).

The host is not particularly limited so long as it can express a functional mutant GSHB. Examples of the host include, for example, bacteria, actinomycetes, yeast, fungi, plant cells, insect cells, and animal cells. Preferred examples of the host include microorganisms such as bacteria and yeast. More preferred examples of the host include bacteria.

Examples of the bacteria include gram-negative bacteria and gram-positive bacteria. Examples of the gram-negative bacteria include, for example, bacteria belonging to the family Enterobacteriaceae, such as *Escherichia* bacteria, *Enterobacter* bacteria, and *Pantoea* bacteria. Examples of the gram-positive bacteria include *Bacillus* bacteria, coryneform bacteria such as *Corynebacterium* bacteria, and Actinomycetes. Examples of the *Escherichia* bacteria include, for example, *Escherichia coli*. Examples of *Escherichia coli* include, for example, *Escherichia coli* K-12 strains such as W3110 strain (ATCC 27325) and MG1655 strain (ATCC 47076); *Escherichia coli* K5 strain (ATCC 23506); *Escherichia coli* B strains such as BL21 (DE3) strain and Rosetta 2(DE3)pLysS strain; and derivative strains thereof. Examples of the coryneform bacteria include, for example, *Colynebacterium glutamicum* and *Corynebacterium ammoniagenes* (*Corynebacterium slationis*).

These strains are available from, for example, the American Type Culture Collection (Address: 12301 Parklawn Drive, Rockville, Md. 20852, P.O. Box 1549, Manassas, Va. 20108, United States of America). That is, registration numbers are given to the respective strains, and the strains can be ordered by using these registration numbers (refer to www(dot)atcc(dot)org/). The registration numbers of the strains are listed in the catalogue of the American Type Culture Collection. These strains can also be obtained from, for example, the depositories at which the strains were deposited. These strains can also be obtained as commercial products.

The method for introducing the mutant GSHB gene into a host is not particularly limited. In the host, the mutant GSHB gene may be harbored in such a manner that it can be expressed under control of a promoter that functions in the host. In the host, the mutant GSHB gene may exist on a vector autonomously replicable out of the chromosome such as a plasmid, or may be introduced into the chromosome. The host may have only one copy of the mutant GSHB gene, or may have two or more copies of the mutant GSHB gene. The host may have only one kind of mutant GSHB gene, or may have two or more kinds of mutant GSHB genes.

The promoter for expressing the mutant GSHB gene is not particularly limited so long as it is a promoter that functions in the host. The "promoter that functions in a host" refers to a promoter that shows a promoter activity in the host. The promoter may be a promoter derived from the host, or a heterologous promoter. The promoter may be the native promoter of the GSHB gene, or may be a promoter of another gene. The promoter is preferably a promoter stronger than the native promoter of the GSHB gene. Examples of strong promoters that function in Enterobacteriaceae bacteria, such as *Escherichia coli*, include, for example, T7 promoter, trp promoter, trc promoter, lac promoter, tac promoter, tet promoter, araBAD promoter, rpoH promoter, msrA promoter, Pml promoter (derived from the genus *Bifidobacterium*), PR promoter, and PL promoter. Examples of strong promoters that function in coryneform bacteria include the artificially modified P54-6 promoter (Appl. Microbiol. Biotechnol., 53, 674-679 (2000)), pta, aceA, aceB, adh, and amyE promoters inducible in coryneform bacteria with acetic acid, ethanol, pyruvic acid, or the like, cspB, SOD, and tuf (EF-Tu) promoters, which are potent promoters capable of providing a large expression amount in coryneform bacteria (Journal of Biotechnology, 104 (2003) 311-323; Appl. Environ. Microbiol., 2005 December; 71

(12):8587-96), as well as lac promoter, tac promoter, and trc promoter. Furthermore, as the stronger promoter, a highly-active type of an existing promoter may also be obtained by using various reporter genes. For example, by making the −35 and −10 regions in a promoter region closer to the consensus sequence, the activity of the promoter can be enhanced (WO00/18935). Examples of highly active-type promoter include various tac-like promoters (Katashkina J I et al., Russian Federation Patent Application No. 2006134574) and pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

Also, a terminator for termination of gene transcription may be located downstream of the mutant GSHB gene. The terminator is not particularly limited so long as it functions in the host. The terminator may be a terminator derived from the host, or a heterogenous terminator. The terminator may be the native terminator of the GSHB gene, or a terminator of another gene. Specific examples of the terminator include, for example, T7 terminator, T4 terminator, fd phage terminator, tet terminator, and trpA terminator.

The mutant GSHB gene can be introduced into a host, for example, by using a vector containing the gene. A vector containing a mutant GSHB gene is also referred to as "expression vector for a mutant GSHB gene" or "recombinant vector for a mutant GSHB gene". The expression vector for the mutant GSHB gene can be constructed by, for example, ligating a DNA fragment containing the mutant GSHB gene with a vector that functions in the host. By transforming the host with the expression vector for the mutant GSHB gene, a transformant into which the vector has been introduced is obtained, i.e. the gene can be introduced into the host. As the vector, a vector autonomously replicable in the cell of the host can be used. The vector is preferably a multi-copy vector. Furthermore, the vector preferably has a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in Enterobacteriaceae bacteria such as *Escherichia coli* include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pACYC, and the broad host spectrum vector RSF1010. Specific examples of vector autonomously replicable in coryneform bacteria include, for example, pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 (Japanese Patent Laid-open (Kokai) No. 3-210184); plasmids pCRY21, pCRY2KE, pCRY2KX, pCRY31, pCRY3KE, and pCRY3KX (Japanese Patent Laid-open (Kokai) No. 2-72876 and U.S. Pat. No. 5,185,262); plasmids pCRY2 and pCRY3 (Japanese Patent Laid-open (Kokai) No. 1-191686); pAJ655, pAJ611, and pAJ1844 (Japanese Patent Laid-open (Kokai) No. 58-192900); pCG1 (Japanese Patent Laid-open (Kokai) No. 57-134500); pCG2 (Japanese Patent Laid-open (Kokai) No. 58-35197); pCG4 and pCG11 (Japanese Patent Laid-open (Kokai) No. 57-183799); pVK7 (Japanese Patent Laid-open (Kokai) No. 10-215883); pVK9 (U.S. 2006-0141588); pVC7 (Japanese Patent Laid-open (Kokai) No. 9-070291); pVS7 (WO2013/069634). When the expression vector is constructed, for example, a mutant GSHB gene having a native promoter region as it is may be incorporated into a vector, a coding region of a mutant GSHB ligated downstream from such a promoter as mentioned above may be incorporated into a vector, or a coding region of a mutant GSHB may be incorporated into a vector downstream from a promoter originally existing in the vector.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

The mutant GSHB gene can also be introduced into, for example, a chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination include, for example, a method using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include repetitive DNAs, and inverted repeats located at the both ends of a transposon. Alternatively, homologous recombination may be performed by using an appropriate sequence on a chromosome such as a gene unnecessary for carrying out the present invention as a target. Furthermore, a gene can also be randomly introduced into a chromosome by using a transposon or Mini-Mu (Japanese Patent Laid-open (Kokai) No. 2-109985, U.S. Pat. No. 5,882,888, EP 805867 B1). When the gene is introduced into a chromosome, for example, a mutant GSHB gene having a native promoter region as it is may be incorporated into a chromosome, a coding region for a mutant GSHB ligated downstream from such a promoter as mentioned above may be incorporated into a chromosome, or a coding region for a mutant GSHB may be incorporated into a chromosome downstream from a promoter originally contained in the chromosome.

Introduction of a gene into a chromosome can be confirmed by, for example, Southern hybridization using a probe having a sequence complementary to a part or the whole of the gene, or PCR using primers prepared on the basis of the nucleotide sequence of the gene.

The method for the transformation is not particularly limited, and conventionally known methods can be used. Examples of transformation method include, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), a method of preparing competent cells from cells which are in the growth phase, followed by transformation with DNA, which has been reported for *Bacillus subtilis* (Duncan, C. H., Wilson, G. A. and Young, F. E., Gene, 1977, 1:153-167), and so forth. Furthermore, as the transformation method, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Furthermore, as the transformation method, the electric pulse method reported for coryneform bacteria (Japanese Patent Laid-open (Kokai) No. 2-207791) can also be used.

The host for expressing the mutant GSHB gene may or may not have the wild-type GSHB gene. It is preferred that the host for expressing the mutant GSHB gene does not have the wild-type GSHB gene. A host not having the wild-type GSHB gene can be obtained by disrupting the wild-type GSHB gene on the chromosome. The method for disrupting a gene will be explained later. For example, a host not having the wild-type GSHB gene but having the mutant GSHB gene can be obtained by replacing the wild-type GSHB gene on the chromosome with the mutant GSHB gene. In order to replace the wild-type GSHB gene with the mutant GSHB gene, there can be used, for example, such methods as the method utilizing the method called "Red driven integration" (Datsenko, K. A, and Wanner, B. L., Proc. Natl. Acad. Sci. USA, 97:6640-6645 (2000)), and an excisive system derived from λ phage (Cho, E. H., Gumport, R. I., Gardner, J. F., J. Bacteriol., 184:5200-5203 (2002)) in combination, and the method for introducing a point mutation into a gene, which applies the foregoing method (Heermann, R et al., Microbial Cell Factories, 7:14 (2008)).

The host for expressing the mutant GSHB gene may also have been modified so that the activity of a protein that participates in decomposition of a γ-glutamyl peptide is reduced. Examples of the protein that participates in decomposition of a γ-glutamyl peptide include γ-glutamyltransferase (GGT). By reducing the activity of GGT, decomposition of γ-Glu-Val and γ-Glu-Val-Gly can be suppressed. The activity of GGT can be reduced by such a means as disrupting a GGT gene encoding GGT. As an example of GGT and GGT gene, the nucleotide sequence of the ggt gene of *Escherichia coli*, and the amino acid sequence of the protein encoded by that gene are shown as SEQ ID NOS: 29 and 30, respectively.

Hereinafter, methods for reducing the activity of a protein will be explained.

The expression "the activity of a protein is reduced" means that the activity of the protein is reduced as compared with a non-modified strain. Specifically, the expression "the activity of a protein is reduced" means that the activity of the protein per cell is reduced as compared with that of a non-modified strain. The term "non-modified strain" used herein refers to a control strain that has not been modified so that the activity of an objective protein is reduced. Examples of the non-modified strain include a wild-type strain and parent strain. Specific examples of the non-modified strain include the type strain of the species to which the host belongs. Specific examples of the non-modified strain also include the strains exemplified above in relation to the description of the host. That is, in an embodiment, the activity of a protein may be reduced as compared with a type strain, i.e. the type strain of the species to which the host belongs. The state that "the activity of a protein is reduced" also includes a state that the activity of the protein has completely disappeared. More specifically, the expression "the activity of a protein is reduced" may mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) encoding the protein or the translation amount of the gene (i.e. the amount of the protein). The state that "the number of molecules of the protein per cell is reduced" also includes a state that the protein does not exist at all. The state that "the function of each molecule of the protein is reduced" also includes a state that the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. The expression "the expression of a gene is reduced" means that the expression of the gene is reduced as compared with a non-modified strain. Specifically, the expression "the expression of a gene is reduced" means that the expression of the gene per cell is reduced as compared with that of a non-modified strain. More specifically, the expression "the expression of a gene is reduced" may mean that the transcription amount of the gene (i.e. the amount of mRNA) is reduced, and/or the translation amount of the gene (i.e. the amount of the protein expressed from the gene) is reduced. The state that "the expression of a gene is reduced" also includes a state that the gene is not expressed at all. The state that "the expression of a gene is reduced" is also referred to as "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as a promoter, Shine-Dalgarno (SD) sequence (also referred to as ribosome-binding site (RBS)), and spacer region between RBS and the start codon of the gene. When an expression control sequence is modified, preferably one or more nucleotides, more preferably two or more nucleotides, particularly preferably three or more nucleotides, of the expression control sequence are modified. The transcription efficiency of a gene can be reduced by, for example, replacing the promoter of the gene on a chromosome with a weaker promoter. The term "weaker promoter" means a promoter providing an attenuated transcription of a gene compared with an inherently existing wild-type promoter of the gene. Examples of weaker promoters include, for example, inducible promoters. That is, an inducible promoter may function as a weaker promoter under a non-induced condition, such as in the absence of the corresponding inducer. Furthermore, a part or the whole of an expression control sequence may be deleted. The expression of a gene can also be reduced by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described later.

The modification for reducing the activity of a protein can also be attained by, for example, disrupting a gene encoding the protein. The expression "a gene is disrupted" means that a gene is modified so that a protein that can normally function is not produced. The state that "a protein that normally functions is not produced" includes a state that the protein is not produced at all from the gene, and a state that the protein of which the function (such as activity or property) per molecule is reduced or eliminated is produced from the gene.

Disruption of a gene can be attained by, for example, deleting the gene on a chromosome. The term "deletion of a gene" refers to deletion of a partial or entire region of the coding region of the gene. Furthermore, the whole of a gene including sequences upstream and downstream from the coding region of the gene on a chromosome may be deleted. The region to be deleted may be any region such as an N-terminal region (region encoding an N-terminal region of a protein), an internal region, or a C-terminal region (region encoding a C-terminal region of a protein), so long as the activity of the protein can be reduced. Deletion of a longer region can usually more surely inactivate the gene. The region to be deleted may be, for example, a region having a length of 10% or more, 20% or more, 30% or more, 40% or more, 50% or more, 60% or more, 70% or more, 80% or more, 90% or more, or 95% or more of the total length of the coding region of the gene. Furthermore, it is preferred that reading frames of the sequences upstream and downstream from the region to be deleted are not the same. Inconsistency of reading frames may cause a frameshift downstream of the region to be deleted.

Disruption of a gene can also be attained by, for example, introducing a mutation for an amino acid substitution (missense mutation), a stop codon (nonsense mutation), addition or deletion of one or two nucleotide residues (frame shift mutation), or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another nucleotide sequence into a coding region of the gene on a chromosome. Site of the insertion may be in any region of the gene, and insertion of a longer nucleotide sequence can usually more surely inactivate the gene. It is preferred that reading frames of the sequences upstream and downstream from the insertion site are not the same. Inconsistency of reading frames may cause a frameshift downstream of the region to be deleted. The other nucleotide sequence is not particularly limited so long as a sequence that reduces or eliminates the activity of the encoded protein is chosen, and examples thereof include, for example, a marker gene such as antibiotic resistance genes, and a gene useful for production of an objective substance.

Particularly, disruption of a gene may be carried out so that the amino acid sequence of the encoded protein is deleted. In other words, the modification for reducing the activity of a protein can be attained by, for example, deleting the amino acid sequence of the protein, specifically, modifying a gene so as to encode a protein of which the amino acid sequence is deleted. The term "deletion of the amino acid sequence of a protein" refers to deletion of a partial or entire region of the amino acid sequence of the protein. In addition, the term "deletion of the amino acid sequence of a protein" means that the original amino acid sequence disappears in the protein, and also includes cases where the original amino acid sequence is changed to another amino acid sequence. That is, for example, a region that was changed to another amino acid sequence by frameshift may be regarded as a deleted region. When the amino acid sequence of a protein is deleted, the total length of the protein is typically shortened, but there can also be cases where the total length of the protein is not changed or is extended. For example, by deletion of a partial or entire region of the coding region of a gene, a region encoded by the deleted region can be deleted in the encoded protein. In addition, for example, by introduction of a stop codon into the coding region of a gene, a region encoded by the downstream region of the introduction site can be deleted in the encoded protein. In addition, for example, by frameshift in the coding region of a gene, a region encoded by the frameshift region can be deleted in the encoded protein. The aforementioned descriptions concerning the position and length of the region to be deleted in deletion of a gene can be applied *mutatis mutandis* to the position and length of the region to be deleted in deletion of the amino acid sequence of a protein.

Such modification of a gene on a chromosome as described above can be attained by, for example, preparing a disruption-type gene modified so that it is unable to produce a protein that normally functions, and transforming a host with a recombinant DNA containing the disruption-type gene to cause homologous recombination between the disruption-type gene and the wild-type gene on a chromosome and thereby substitute the disruption-type gene for the wild-type gene on the chromosome. In this procedure, if a marker gene selected according to the characteristics of the host such as auxotrophy is included in the recombinant DNA, the operation becomes easier. Examples of the disruption-type gene include a gene of which a partial or entire region of the coding region is deleted, gene including a missense mutation, gene including a nonsense mutation, gene including a frame shift mutation, and gene inserted with an insertion sequence such as a transposon or marker gene. The structure of the recombinant DNA to be used for homologous recombination is not particularly limited, so long as it causes homologous recombination in a desired manner. For example, a host can be transformed with a linear DNA comprising the disruption-type gene and further comprising upstream and downstream sequences of the wild-type gene on the chromosome at the respective termini of the disruption-type gene, so that homologous recombination can occur at upstream and downstream sides of the wild-type gene, to thereby replace the wild-type gene with the disruption-type gene in one step. The protein encoded by the disruption-type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

Modification for reducing activity of a protein can also be attained by, for example, a mutagenesis treatment. Examples of the mutagenesis treatment include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

Such methods for reducing the activity of a protein as mentioned above may be used independently or in any combination.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA include Northern hybridization, RT-PCR, and so forth (Molecular Cloning, Cold Spring Harbor Laboratory Press, Cold Spring Harbor (USA), 2001). The amount of mRNA may be reduced to, for example, 50% or less, 20% or less, 10% or less, 5% or less, or 0% of that of a non-modified strain.

A reduction in the amount of a protein can be confirmed by carrying out SDS-PAGE, and confirming the intensity of a separated protein band. A reduction in the amount of a protein can also be confirmed by Western blotting using antibodies (Molecular Cloning, Cold Spring Harbor Laboratory Press, Cold Spring Harbor (USA) 2001). The amount of the protein (such as the number of molecules of the protein per cell) may be reduced to, for example, 50% or less, 20% or less, 10% or less, 5% or less, or 0% of that of a non-modified strain.

Disruption of a gene can be confirmed by determining nucleotide sequence of a part or the whole of the gene, restriction enzyme map, full length, or the like of the gene depending on the means used for the disruption.

By culturing the host obtained as described above, into which the mutant GSHB gene has been introduced, the mutant GSHB can be expressed. Conditions for culture of the host and induction of gene expression may be appropriately selected depending on various conditions such as type of marker, type of promoter, and type of the host. The culture medium used for the culture is not be particularly limited, so long as the host can proliferate in the culture medium and express the mutant GSHB. As the culture medium, for example, a usual culture medium that contains a carbon source, nitrogen source, sulfur source, inorganic ions, and other organic components as required can be used.

Examples of the carbon source include saccharides such as glucose, fructose, sucrose, molasses, and starch hydrolysate, alcohols such as glycerol and ethanol, and organic acids such as fumaric acid, citric acid, and succinic acid.

Examples of the nitrogen source include inorganic ammonium salts such as ammonium sulfate, ammonium chloride, and ammonium phosphate, organic nitrogen such as soybean hydrolysate, ammonia gas, and aqueous ammonia.

Examples of the sulfur source include inorganic sulfur compounds, such as sulfates, sulfites, sulfides, hyposulfites, and thiosulfates.

Examples of the inorganic ions include calcium ion, magnesium ion, manganese ion, potassium ion, iron ion, and phosphoric acid ion.

Examples of the other organic components include organic trace amount nutrients. Examples of the organic trace amount nutrients include required substances such as vitamin $B_1$, yeast extract containing such substances, and so forth.

Culture temperature may be, for example, 20 to 45° C., preferably 24 to 45° C. The culture is preferably performed as aeration culture. In the aeration culture, oxygen concentration may be adjusted to 5 to 50%, preferably about 10%, to the saturated concentration. The pH during the culture is preferably 5 to 9. For adjusting the pH, inorganic or organic acidic or alkaline substances, such as calcium carbonate, ammonia gas, and aqueous ammonia, can be used.

By performing the culture preferably for about 10 to 120 hours under such conditions as mentioned above, a culture broth containing the mutant GSHB is obtained. The mutant GSHB can be accumulated in, for example, microbial cells of the host. The term "microbial cell" may be appropriately read as "cell" depending on type of the host. Depending on the host to be used and design of the mutant GSHB gene, it is also possible to accumulate the mutant GSHB in the periplasm, or to produce the mutant GSHB out of the cells by secretory production.

The mutant GSHB may be used in a state that it is contained in microbial cells or the like, or may be separated and purified from microbial cells or the like to be used as a crude enzyme fraction or a purified enzyme, as required.

That is, for example, when the mutant GSHB is accumulated in microbial cells of the host, by subjecting the cells to disruption, lysis, extraction, etc. as required, the mutant GSHB can be collected. The microbial cells can be collected from the culture broth by centrifugation or the like. Disruption, lysis, extraction, etc. of the cells can be performed by known methods. Examples of such methods include, for example, disruption by ultrasonication, disruption in Dyno-Mill, disruption in bead mill, disruption with French press, and lysozyme treatment. Any one of these methods may be independently used, or two or more of them may be used in combination as required. Also, for example, when the mutant GSHB is accumulated in the culture medium, a culture supernatant can be obtained by centrifugation or the like, and the mutant GSHB can be collected from the culture supernatant.

The mutant GSHB can be purified by known methods used for purification of enzymes. Examples of such methods include, for example, ammonium sulfate fractionation, ion exchange chromatography, hydrophobic chromatography, affinity chromatography, gel filtration chromatography, and isoelectric precipitation. Any one of these methods may be independently used, or two or more of them may be used in combination as required. The mutant GSHB may be purified to a desired extent. For example, when the mutant GSHB is contaminated with an ingredient that participates in decomposition of γ-glutamyl peptides, such as GGT, it is preferable to remove such an ingredient.

The purified mutant GSHB can be used as the "mutant GSHB" in the method of the present invention. The mutant GSHB may be used in a free form, or may be used as an immobilized enzyme immobilized on a solid phase of resin etc.

Not only the purified mutant GSHB, but also an arbitrary fraction containing the mutant GSHB may be used as the "mutant GSHB" in the method of the present invention. Such a fraction containing the mutant GSHB is not particularly limited, so long as it contains the mutant GSHB so that the mutant GSHB can act on γ-Glu-Val and Gly. Examples of such a fraction include, for example, a culture broth of a host having the mutant GSHB gene (i.e. host having the mutant GSHB), microbial cells collected from such a culture broth (i.e. cultured microbial cells), processed products of such microbial cells such as disruption product of the cells, lysate of the cells, extract of the cells (i.e. cell-free extract), and immobilized cells obtained by immobilizing such cells as mentioned above on a carrier such as acrylamide and carrageenan, culture supernatant collected from such a culture broth, partially purified products (i.e. roughly purified products) of them, and combinations of them. These fractions each may be used alone, or may be used together with a purified mutant GSHB.

<3> γ-Glutamylvaline Synthetase (GSHA) and Production Thereof

The term "γ-glutamylvaline synthetase" refers to a protein having an activity for catalyzing a reaction of generating γ-Glu-Val, ADP, and phosphate using Glu, Val, and ATP as the substrates. This activity is also referred to as "γ-glutamylvaline synthetase activity" or "γ-Glu-Val synthesis activity". In the present invention, γ-glutamylvaline synthetase is also referred to as "GSHA". In the present invention, a gene encoding a GSHA is also referred to as "γ-glutamylvaline synthetase gene (GSHA gene)". GSHA also includes enzymes that have been conventionally referred to as glutamate-cysteine ligase and have the γ-glutamylvaline synthetase activity.

Furthermore, an activity for catalyzing a reaction of generating γ-Glu-Gly, ADP, and phosphate using Glu, Gly, and ATP as the substrates is also referred to as "γ-glutamylglycine synthetase activity" or "γ-Glu-Gly synthesis activity".

Furthermore, an activity for catalyzing a reaction of generating γ-Glu-Cys, ADP, and phosphate using Glu, Cys, and ATP as the substrates is also referred to as "γ-glutamylcysteine synthetase activity" or "γ-Glu-Cys synthesis activity".

These enzymatic activities each can be measured on the basis of, for example, generation of the corresponding γ-glutamyl dipeptide upon allowing an enzyme to act on the substrates under appropriate conditions. These enzymatic activities each can be measured, for example, in the presence of a divalent metal ion. Examples of the divalent metal ion include $Mg^{2+}$ and $Mn^{2+}$.

The γ-glutamylvaline synthetase activity can be measured by adding an appropriate amount of enzyme to a reaction mixture (10 mM Glu, 10 mM Val, 10 mM ATP, 10 mM $MnSO_4$, and 100 mM Tris-HCl, pH 7.0-9.0), performing the reaction at 30° C. for 30 minutes, and calculating the activity on the basis of the amount of generated γ-Glu-Val. In the present invention, the enzymatic activity for generating 1 μmol of γ-Glu-Val in 1 minute under the aforementioned conditions is defined as 1 U of the γ-glutamylvaline synthetase activity (in the presence of $Mn^{2+}$). Similarly, the γ-glutamylglycine synthetase activity can be measured by adding an appropriate amount of enzyme to a reaction mixture (10 mM Glu, 10 mM Gly, 10 mM ATP, 10 mM $MnSO_4$, and 100 mM Tris-HCl, pH 7.0-9.0), performing the reaction at 30° C. for 30 minutes, and calculating the activity on the basis of the amount of generated γ-Glu-Gly. In the present invention, the enzymatic activity for generating 1 μmol of γ-Glu-Gly in 1 minute under the aforementioned conditions is defined as 1 U of the γ-glutamylglycine synthetase activity (in the presence of $Mn^{2+}$).

Furthermore, by using a reaction mixture containing 10 mM $MgSO_4$ instead of 10 mM $MnSO_4$, the γ-glutamylvaline synthetase activity and γ-glutamylglycine synthetase activity in the presence of $Mg^{2+}$ can be measured. That is, the enzymatic activity for generating 1 μmol of γ-Glu-Val in 1 minute under the aforementioned conditions using this reaction mixture is defined as 1 U of the γ-glutamylvaline synthetase activity (in the presence of $Mg^{2+}$). Similarly, the enzymatic activity for generating 1 μmol of γ-Glu-Gly in 1 minute under the aforementioned conditions using this reaction mixture is defined as 1 U of the γ-glutamylglycine synthetase activity (in the presence of $Mg^{2+}$).

A ratio of the γ-glutamylvaline synthetase activity (specifically, the specific activity) to the γ-glutamylglycine synthetase activity (specifically, the specific activity), i.e. the specific activity of γ-glutamylvaline synthetase activity/the specific activity of γ-glutamylglycine synthetase activity, is also referred to as "Val-selectivity". The Val-selectivity can be obtained by measuring the γ-glutamylvaline synthetase activity and γ-glutamylglycine synthetase activity, and calculating the ratio therefrom.

The GSHA may have or may not have an activity of generating a γ-glutamyl dipeptide other than γ-glutamylvaline, so long as it has the γ-glutamylvaline synthetase activity. That is, for example, the GSHA may have or may not have the γ-glutamylcysteine synthetase activity. Also, for example, the GSHA may have or may not have the γ-glutamylglycine synthetase activity. It is preferred that the GSHA does not have the γ-glutamylglycine synthetase activity. Methods for measuring the γ-glutamylvaline synthetase activity and the γ-glutamylglycine synthetase activity are as described above. It is sufficient that the GSHA has the γ-glutamylvaline synthetase activity under appropriate conditions. The GSHA may have the γ-glutamylvaline synthetase activity, for example, in the presence of $Mg^{2+}$ or $Mn^{2+}$, or particularly in the presence of $Mg^{2+}$. The GSHA may have the γ-glutamylvaline synthetase activity, for example, at least at one pH within pH7.0-9.0, or particularly at pH9.0.

The GSHA may have a high Val-selectivity. The Val-selectivity of the GSHA may be, for example, 2.0 or higher, 3.0 or higher, 5.0 or higher, 10 or higher, 15 or higher, or 20 or higher. The Val-selectivity of the GSHA may be, for example, 10,000,000 or lower, 1,000,000 or lower, 100,000 or lower, 10,000 or lower, 1,000 or lower, 100 or lower, or 50 or lower. The Val-selectivity of the GSHA may be, for example, within a range defined by any combination of the aforementioned ranges. The GSHA may show the Val-selectivity exemplified above under appropriate conditions. The GSHA may show the Val-selectivity exemplified above, for example, in the presence of $Mg^{2+}$ or $Mn^{2+}$, or particularly in the presence of $Mg^{2+}$. The GSHA may show the Val-selectivity exemplified above, for example, at least at one pH within pH7.0-9.0, or particularly at pH9.0.

In particular, by using a GSHA showing a high Val-selectivity in combination with the mutant GSHB, it is expected that γ-glutamylvalylglycine can be efficiently produced from Glu, Val, and Gly with reduced by-production of γ-glutamylglycine.

The origin of the GSHA is not particularly limited, and GSHAs derived from any organisms such as microorganisms, plants, and animals can be used.

Examples of the GSHA include, for example, GSHAs of *Kocuria* bacteria, *Micrococcus* bacteria, and *Corynebacterium* bacteria (WO2015/133547). Examples of the *Kocuria* bacteria include *Kocuria rosea*, and *Kocuria rhizophila*. Examples of the *Micrococcus* bacteria include *Micrococcus luteus*. Examples of the *Corynebacterium* bacteria include *Corynebacterium glutamicum*. That is, the GSHA may be, for example, a protein derived from such microorganisms as mentioned above.

The nucleotide sequence of the GSHA gene of *Kocuria rosea* (AJ3132) and the amino acid sequence of the protein encoded by the gene are shown as SEQ ID NOS: 21 and 22, respectively. The nucleotide sequence of the GSHA gene of the *Kocuria rhizophila* DC2201 strain (ATCC 9341) and the amino acid sequence of the protein encoded by the gene are shown as SEQ ID NOS: 23 and 24, respectively. The nucleotide sequence of the GSHA gene of the *Micrococcus luteus* NCTC2665 strain (ATCC 15307) and the amino acid sequence of the protein encoded by the gene are shown as SEQ ID NOS: 25 and 26, respectively. That is, the GSHA may be, for example, a protein having the amino acid sequence of the GSHA exemplified above (for example, the amino acid sequence of SEQ ID NO: 22, 24, or 26). Furthermore, the GSHA may be, for example, a protein encoded by a gene having the nucleotide sequence of the GSHA gene exemplified above (for example, the nucleotide sequence of SEQ ID NO: 21, 23, or 25).

The GSHA may also be a variant of the GSHA exemplified above (for example, a protein having the amino acid sequence shown as SEQ ID NO: 22, 24, or 26), so long as the variant has the γ-glutamylvaline synthetase activity. Similarly, the GSHA gene may also be a variant of the GSHA gene exemplified above (for example, a gene having the nucleotide sequence shown as SEQ ID NO: 21, 23, or 25), so long as the variant encodes a protein having the γ-glutamylvaline synthetase activity. The descriptions concerning variants of the mutant GSHB gene and mutant GSHB described above can be applied *mutatis mutandis* to variants of the GSHA gene and GSHA. The enzymatic characteristics of the variant, such as substrate specificity, requirement for divalent metal ions, and pH dependency, each may be or may not be identical to those of the original protein, so long as the variant has the γ-glutamylvaline synthetase activity. For example, the variant may have or may not have an activity of generating a γ-glutamyl dipeptide other than γ-glutamylvaline. Also, the variant may show the Val-selectivity exemplified above.

Examples of the GSHA also include, for example, the mutant glutamate-cysteine ligase (mutant GSHA) disclosed in WO2015/115612.

In the present invention, the term "mutant glutamate-cysteine ligase (mutant OSHA)" refers to a glutamate-cysteine ligase having a "specific mutation". In the present invention, a gene encoding a mutant GSHA is also referred to as "mutant glutamate-cysteine ligase gene (mutant GSHA gene)". The "specific mutation" will be described later.

In the present invention, a glutamate-cysteine ligase not having the "specific mutation" is also referred to as "wild-type glutamate-cysteine ligase (wild-type GSHA)". In the present invention, a gene encoding a wild-type GSHA is also referred to as "wild-type glutamate-cysteine ligase gene (wild-type GSHA gene)". The term "wild-type" is used for convenience for distinguishing the "wild-type" ones from the "mutant" ones, and the wild-type gene or enzyme is not limited to a naturally occurring one, so long as the gene or enzyme does not have the "specific mutation".

Examples of the wild-type GSHA include the GshA protein encoded by the gshA gene of *Escherichia coli*. The nucleotide sequence of the gshA gene of the *Escherichia coil* K-12 MG1655 strain and the amino acid sequence of the protein encoded by this gene are shown as SEQ ID NOS: 27 and 28, respectively. That is, the wild-type GSHA may be, for example, a protein encoded by a gene having the nucleotide sequence shown as SEQ ID NO: 27. The wild-type GSHA may also be, for example, a protein having the amino acid sequence shown as SEQ ID NO: 28.

The wild-type GSHA may be a variant of the wild-type GSHA exemplified above (for example, a protein having the amino acid sequence shown as SEQ ID NO: 28), so long as it does not have the "specific mutation". The aforementioned descriptions concerning variants of the wild-type GSHB gene and wild-type GSHB described above can be applied *mutatis mutandis* to variants of the wild-type GSHA gene and wild-type GSHA.

The wild-type GSHA may typically be a protein having the γ-glutamylcysteine synthetase activity. However, in the present invention, so long as the corresponding mutant GSHA has the γ-glutamylvaline synthetase activity, the wild-type GSHA may have the γ-glutamylcysteine synthetase activity, γ-glutamylvaline synthetase activity, γ-glutamylglycine synthetase activity, or any combination of these activities, or may have none of these activities.

The mutant GSHA has the "specific mutation" in the amino acid sequence of the wild-type GSHA. That is, for example, the mutant GSHA may be a protein having the amino acid sequence shown as SEQ ID NO: 28, but including the "specific mutation". The mutant GSHA may also be, for example, a protein having the amino acid sequence shown as SEQ ID NO: 28, but including the "specific mutation", further including substitution, deletion, insertion, and/or addition of one or several amino acid residues at a site other than that of the "specific mutation", and having the γ-glutamylvaline synthetase activity. In other words, the mutant GSHA may be a protein having an amino acid sequence identical to that of the wild-type GSHA, except that it has the "specific mutation". For example, the mutant GSHA may be a protein having the amino acid sequence shown as SEQ ID NO: 28, except that it has the "specific mutation". The mutant GSHA may also be, for example, a protein having the amino acid sequence shown as SEQ ID NO: 28, but including substitution, deletion, insertion, and/or addition of one or several amino acid residues, and having the γ-glutamylvaline synthetase activity, except that it has the "specific mutation". The mutant GSHA may also be, for example, a protein having an amino acid sequence showing a homology of 80% or higher, preferably 90% or higher, more preferably 95% or higher, still more preferably 97% or higher, particularly preferably 99% or higher, to the amino acid sequence shown as SEQ ID NO: 28, and having the γ-glutamylvaline synthetase activity, except that it has the "specific mutation".

The "specific mutation" refers to a mutation that imparts a characteristic suitable for generation of γ-glutamylvaline to the wild-type GSHA, when it is introduced into the wild-type GSHA. That is, because of having the "specific mutation", the mutant GSHA has a characteristic suitable for generation of γ-glutamylvaline, compared with the wild-type GSHA. Examples of the characteristic suitable for generation of γ-glutamylvaline include, for example, increased γ-glutamylvaline synthetase activity (specifically, the specific activity), reduced γ-glutamylglycine synthetase activity (specifically, the specific activity), increased Val-selectivity, and a combination thereof. The γ-glutamylvaline synthetase activity (specifically, the specific activity) of the mutant GSHA, for example, may be 1.1 times or more, 1.5 times or more, 2 times or more, 5 times or more, 7 times or more, 10 times or more, or 20 times or more of that of the wild-type GSHA, may be 10,000,000 times or less, 1,000,000 times or less, 100,000 times or less, 10,000 times or less, 1,000 times or less, 100 times or less, 50 times or less of that of the wild-type GSHA, or may be within a range defined by any combination of the aforementioned ranges.

Examples of the "specific mutation" include a mutation corresponding to a mutation at one or more amino acid residues selected from the followings:

L135, Q144, Y241, N243, Y300.

In the aforementioned description, the numerals indicate the positions in the amino acid sequence of the wild-type GSHA shown as SEQ ID NO: 28, and the letters on the left side of the numerals indicate the amino acid residues at the respective positions in the amino acid sequence of the wild-type GSHA shown as SEQ ID NO: 28 (namely, the amino acid residues before being mutated, indicated with one-letter code). For example, "L135" indicates the Leu residue at position 135 in the amino acid sequence of the wild-type GSHA shown as SEQ ID NO: 28.

As for the aforementioned mutation, the amino acid residues after substitution may be any amino acid residues other than the original amino acid residues, so long as the mutant GSHA has the γ-glutamylvaline synthetase activity. Specific examples of the amino acid residue after the substitution include K (Lys), R (Arg), H (His), A (Ala), V (Val), L (Leu), I (Ile), G (Gly), S (Ser), T (Thr), P (Pro), F (Phe), W (Trp), Y (Tyr), C (Cys), M (Met), D (Asp), E (Glu), N (Asn), and Q (Gln), which should be other than the original amino acid residues.

Specific examples of the "specific mutation" include a mutation corresponding to one or more mutations selected from the followings. That is, the "specific mutation" may include a mutation corresponding to one or more mutations selected from the followings. The "specific mutation" may be, for example, a mutation corresponding to any one of mutation selected from the followings, or may be a mutation corresponding to a combination of two or more mutations selected from the followings. The "specific mutation" may also be, for example, a mutation corresponding to a combination of one or more mutations selected from the followings, and a mutation other than the foregoing mutation at one or more amino acid residues selected from L135, Q144, Y241, N243, and Y300.

L135(I, F, M, V, G, A, W, K, H, R, C, N, S, T),
Q144(F, A, N, S, D, T, R, H, G, K, Y, W, C, M, P, V, L, I),
Y241(A),
N243(I, W, K, R, H),
Y300(A, H, R, K).

In the aforementioned descriptions, the meanings of the numerals and the letters on the left side of the numerals are the same as those described above. The letters in the parentheses on the right side of the numerals indicate the amino acid residues (one-letter code) after being mutated. Namely, for example, "L135(I, F, M, V, G, A, W, K, H, R, C, N, S, T)" means a mutation that the Leu residue at position 135 in the amino acid sequence of the wild-type GSHA shown as SEQ ID NO: 28 is replaced with any one of amino acid residues of Ile, Phe, Met, Val, Gly, Ala, Trp, Lys, His, Arg, Cys, Asn, Ser, and Thr. The amino acid residues after being mutated may also be mentioned without parenthesis. That is, for example, "L135I" means a mutation that the Leu residue at position 135 in the amino acid sequence of the wild-type GSHA shown as SEQ ID NO: 28 is replaced with an Ile residue.

Combination of the mutations is not particularly limited. Specific examples of combination of the mutations include the following combinations:

L135I/Q144R, L135I/Q144D, L135I/Q144A, L135I/Q144L, L135I/N243W, L135I/N243F, L135F/Q144A, L135F/N243W, L135M/Q144R, L135M/Q144A, L135M/Q144L, L135M/N243W, L135M/N243F, L135M/Q144H, L135M/Q144N, L135M/N243Y, L135M/N243R, L135M/N243C, L135V/Q144R, L135V/Q144D, L135V/Q144A, L135V/Q144L, L135V/Q144V, L135V/Q144K, L135V/Q144C, L135V/Q144T, L135H/Q144R, L135G/Q144L, L135A/Q144L, L135V/N243W, LI 35V/N243F, L135V/N243P, Q144R/N243W, Q144R/N243F, Q144D/N243W, Q144D/N243F, Q144A/N243W, Q144A/N243F, Q144L/N243W, Q144L/N243F, L135M/Q144F, L135M/N243A, L135V/N243G, L135V/N243A, L135V/N243L, L135V/N243Y, L135V/N243K, L135V/N243R, L135V/N243H, L135V/N243D, L135V/N243E, L135V/N243C, L135V/N243Q, L135V/N243S, L135V/N243T, L135V/Q144I, L135V/Q144P, L135V/Q144W, L135V/Q144H, L135V/Q144E, L135V/Q144N, L135V/Q144S, L135K/Q144L, L135H/Q144L, L135D/Q144L, L135C/Q144L, L135Q/Q144L, L135N/Q144L, L135S/Q144L, L135T/Q144L.

In the aforementioned descriptions, the meanings of the numerals and the letters on the left and right sides of the numerals are the same as those described above. In the aforementioned descriptions, two ore more mutations separated with "/" indicate a double or more multiple mutation. That is, for example, "L135I/Q144R" indicates a double mutation of L135I and Q144R.

Also, examples of mutations with which a significant increase of the γ-glutamylvaline synthetase activity (specifically, the specific activity) was observed in the Examples of WO2015/115612 include the following mutations:

L135(I, M, V, G, A, K, H, C, N, S, T),
Q144(F, A, S, D, T, R, H, K, Y, W, C, M, P, V, L, I),
N243(R, H),
Y300(R, K),
L135I/Q144R, L135I/Q144D, L135I/Q144A, L135I/Q144L, L135I/N243W, L135I/N243F, L135F/Q144A, L135M/Q144R, L135M/Q144A, L135M/Q144L, L135M/N243W, L135M/Q144H, L135M/Q144N, L135M/N243C, L135V/Q144R, L135V/Q144D, L135V/Q144A, L135V/Q144L, L135V/Q144V, L135V/Q144K, L135V/Q144C, L135V/Q144T, L135H/Q144R, L135G/Q144L, L135A/Q144L, L135V/N243W, L135V/N243F, L135V/N243P, Q144R/N243W, Q144D/N243W, Q144A/N243W, Q144A/N243F, Q144L/N243W, Q144L/N243F, L135M/Q144F, L135M/N243A, L135V/N243G, L135V/N243A, L135V/N243L, L135V/N243Y, L135V/N243K, L135V/N243R, L135V/N243H, L135V/N243D, L135V/N243E, L135V/N243C, L135V/N243Q, L135V/N243S, L135V/N243T, L135V/Q144P, L135V/Q144W, L135V/Q144H, L135V/Q144E, L135V/Q144N, L135V/Q144S, L135D/Q144L, L135C/Q144L, L135N/Q144L, L135S/Q144L, L135T/Q144L.

A "mutation corresponding to a mutation of an amino acid residue at position n in the amino acid sequence shown as SEQ ID NO: 28" in the amino acid sequence of any chosen wild-type GSHA means a mutation at an amino acid residue corresponding to the amino acid residue at position n in the amino acid sequence shown as SEQ ID NO: 28. That is, for example, a "mutation corresponding to L135I" indicates a mutation that an amino acid residue corresponding to the Leu residue at position 135 (L135) in the amino acid sequence of wild-type GSHA shown as SEQ ID NO: 28 is replaced with an Ile residue. The "amino acid residue corresponding to L135" mentioned here may typically be a Leu residue, but may not be a Leu residue. Namely, for example, the "mutation corresponding to L135I" is not limited to a mutation that when the "amino acid residue corresponding to L135" is a Leu residue, the Leu residue is replaced with an Ile residue, but includes a mutation that when the "amino acid residue corresponding to L135" is Lys, Arg, His, Ala, Val, Gly, Ser, Thr, Pro, Phe, Trp, Tyr, Cys, Met, Asp, Glu, Asn, or Gln residue, this amino acid residue is replaced with an Ile residue. The same shall apply to the other mutations.

The descriptions concerning the position of the mutation in the mutant GSHB described above can be applied *mutatis mutandis* to the position of the "amino acid residue corresponding to the amino acid residue at position n in the amino acid sequence shown as SEQ ID NO: 28" in the amino acid sequence of any chosen wild-type GSHA.

The GSHA may have another amino acid sequence in addition to such an amino acid sequence of the GSHA as exemplified above. The descriptions concerning the "another amino acid sequence" in the mutant GSHB can be applied *mutatis mutandis* to the "another amino acid sequence" in the GSHA.

The GSHA can be produced by making a host having the GSHA gene express the GSHA gene. Such a host having the GSHA gene may be one obtained by introducing the GSHA gene into an appropriate host, or may be one inherently having the GSHA gene. A host having a GSHA gene is also referred to as "host having a GSHA". Examples of such a host inherently having the GSHA gene include microorganisms from which the GSHAs exemplified above are derived. The host inherently having the GSHA gene may have been modified so that the expression of the GSHA gene is increased. Examples of the means for increasing the expression of the GSHA gene include increasing the copy number of the GSHA gene, and improving the transcription efficiency of the GSHA gene. The copy number of the GSHA gene can be increased by introducing the GSHA gene into a host. The aforementioned descriptions concerning acquisition and introduction of the mutant GSHB gene can be applied *mutatis mutandis* to acquisition and introduction of the GSHA gene. The GSHA gene to be introduced may be a gene derived from the host, or heterogenous gene. The transcription efficiency of the GSHA gene can be improved by replacing the promoter of the GSHA gene with a stronger promoter. As such a stronger promoter, the strong promoters mentioned above can be used. The host for expressing the GSHA gene may also have been modified so that the activity of a protein that participates in decomposition of γ-glutamyl peptides, such as γ-glutamyltransferase (GGT), is reduced. The GSHA can also be produced by expressing the GSHA gene in a cell-free protein synthesis system.

The aforementioned descriptions concerning production of the mutant GSHB using a host into which the mutant GSHB gene has been introduced can be applied *mutatis mutandis* to the production of GSHA using a host having the GSHA gene. The produced GSHA (such as a purified GSHA and a fraction containing the GSHA) can be used as the "GSHA" in the method of the present invention. The GSHA may be independently produced, or may be produced together with the mutant GSHB. For example, the GSHA and the mutant GSHB can be produced together by making a host having both the GSHA gene and the mutant GSHA gene express these genes.

<4> Method for Producing γ-glutamylvalylglycine (γ-Glu-Val-Gly)

The present invention provides a method for producing γ-Glu-Val-Gly (CAS 38837-70-6; also referred to as "Gluvalicine") using the mutant GSHB. This method is also referred to as "method of the present invention". The structural formula of γ-Glu-Val-Gly is shown in the Formula (I) below.

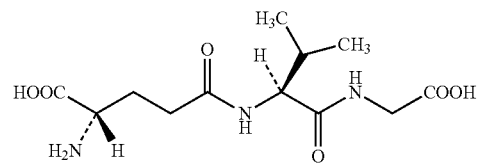

<Formula (I)>

In the method of the present invention, specifically, γ-Glu-Val-Gly can be produced by using an appropriate combination of the GSHA, the mutant GSHB, a microorganism having the GSHA, a microorganism having the mutant GSHB, a microorganism having the GSHA and the mutant GSHB, Glu, Val, Gly, γ-Glu-Val, etc.

In the method of the present invention, the GSHA and the mutant GSHB are also collectively referred to as "enzymes". A microorganism having the GSHA, a microorganism having the mutant GSHB, and a microorganism having the GSHA and the mutant GSHB are also collectively referred to as "microorganisms". Glu, Val, and Gly are also collectively referred to as "amino acids". γ-Glu-Val and γ-Glu-Val-Gly are also collectively referred to as "peptides". Glu, Val, Gly, and γ-Glu-Val are also collectively referred to as "substrates". The "substrates" may further include ATP, unless otherwise stated. A reaction of an enzyme and a substrate corresponding to the enzyme is also referred to as "enzymatic reaction".

As each of the amino acids or γ-Glu-Val, a commercial product may be used, or one appropriately prepared and obtained may be used. Methods for producing an amino acid or γ-Glu-Val are not particularly limited, and, for example, known methods can be used. An amino acid or γ-Glu-Val can be produced by, for example, chemical synthesis, enzymatic reaction, or a combination of them. An amino acid or γ-Glu-Val can also be produced by, for example, culturing a microorganism having an ability to produce the amino acid or γ-Glu-Val, and collecting the amino acid or γ-Glu-Val from culture. As a microorganism having an ability to produce an amino acid, for example, such an amino acid-producing microorganism as described later can be used. As a microorganism having an ability to produce γ-Glu-Val, for example, a microorganism having the GSHA can be used. An amino acid or γ-Glu-Val can also be produced by, for example, collecting the amino acid or γ-Glu-Val from agricultural, aquatic, and livestock products containing the amino acid or γ-Glu-Val. As each of the amino acids or γ-Glu-Val, a purified product purified to a desired extent may be used, or a material containing the amino acid or γ-Glu-Val may be used. Such a material containing an amino acid or γ-Glu-Val is not particularly limited so long as it contains an amino acid or γ-Glu-Val in such a manner that an enzyme can act on the amino acid or γ-Glu-Val. Specific examples of the material containing an amino acid or γ-Glu-Val include, for example, a culture broth obtained by culturing a microorganism having an ability to produce the amino acid or γ-Glu-Val, a culture supernatant separated from the culture broth, cells separated from the culture broth, and processed products thereof such as concentrates (concentrated liquids) thereof and concentrated and dried products thereof.

Specifically, for example, a reaction of Glu and Val can be carried out to generate γ-Glu-Val by using the GSHA. Specifically, for example, γ-Glu-Val can be produced from Glu and Val by fermentation using a microorganism having the GSHA. Regarding specific production conditions, the conditions for carrying out each step of the enzymatic method and fermentative method described later can be used as a reference.

In the method of the present invention, the amino acids and peptides each may be a free compound, salt thereof, or mixture of them, unless otherwise stated. That is, the term "amino acid" may mean amino acid in the form of free compound, salt thereof, or mixture of them, unless otherwise stated. The term "peptide" may mean peptide in the form of free compound, salt thereof, or mixture of them, unless otherwise stated. The salt is not particularly limited so long as it is a chemically acceptable salt. When the produced γ-Glu-Val-Gly is used for oral use (for example, use as an additive for foods and drinks), the salt of γ-Glu-Val-Gly is not particularly limited so long as it is a chemically acceptable edible salt. Specific examples of the "chemically acceptable edible salt" include, for acidic groups such as carboxyl group, for example, ammonium salts, salts with alkali metals such as sodium and potassium, salts with alkaline earth metals such as calcium and magnesium, aluminum salts, zinc salts, salts with organic amines such as triethylamine, ethanolamine, morpholine, pyrrolidine, piperidine, piperazine, and dicyclohexylamine, and salts with basic amino acids such as arginine and lysine. Specific examples of the "chemically acceptable edible salt" include, for basic groups, for example, salts with inorganic acids such as hydrochloric acid, sulfuric acid, phosphoric acid, nitric acid, and hydrobromic acid, salts with organic carboxylic acids such as acetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid, and malic acid, and salts with organic sulfonic acid such as methanesulfonic acid, benzenesulfonic acid, and p-toluenesulfonic acid. As the salt, one kind of salt may be used, or two or more kinds of salts may be used in combination.

<4-1> Enzymatic Method

The present invention provides a method for enzymatically producing γ-Glu-Val-Gly by using the mutant GSHB. This method is also referred to as "method for producing γ-Glu-Val-Gly of the present invention (enzymatic method)".

In the present invention, a reaction of γ-Glu-Val and Gly can be carried out to generate γ-Glu-Val-Gly by using the mutant GSHB. That is, an embodiment of the method for producing γ-Glu-Val-Gly of the present invention (enzymatic method) (also referred to as the "first embodiment") is a method for producing γ-Glu-Val-Gly, which comprises (B) a step of allowing the mutant GSHB to act on γ-Glu-Val and Gly to generate γ-Glu-Val-Gly.

The first embodiment may further comprise (A) a step of generating γ-Glu-Val. In this case, γ-Glu-Val generated in the step (A) can be used as γ-Glu-Val in the step (B). That is, the first embodiment may be, for example, a method for producing γ-Glu-Val-Gly, which comprises (A) a step of generating γ-Glu-Val, and (B) a step of allowing the mutant GSHB to act on γ-Glu-Val generated in the step (A) and Gly to generate γ-Glu-Val-Gly. The step (A) can be carried out by such a method as described above. The step (A) may be, for example, a step of allowing the GSHA to act on Glu and Val to generate γ-Glu-Val, or a step of culturing a microorganism having the GSHA in a culture medium to generate γ-Glu-Val from Glu and Val. The first embodiment may specifically be, for example, a method for producing γ-Glu-Val-Gly, which comprises (A) a step of allowing the GSHA to act on Glu and Val to generate γ-Glu-Val, and (B) a step of allowing the mutant GSHB to act on γ-Glu-Val generated in the step (A) and Gly to generate γ-Glu-Val-Gly. Although the first embodiment is explained hereinafter with assuming a case where the step (A) is a step of allowing the GSHA to act on Glu and Val to generate γ-Glu-Val, the explanation can also be applied *mutatis mutandis* to cases of carrying out the step (A) by other methods.

In the first embodiment, the step (A) and the step (B) may be carried out separately, or may be carried out simultaneously during a partial period or the whole period of the steps. That is, for example, the step (A) and the step (B) may be started simultaneously, or the step (B) may be started while the step (A) is in progress or after the step (A) is completed. The step (A) and the step (B) can be simultaneously started by making the GSHA, the mutant GSHB, Glu, Val, and Gly coexist in a reaction system at the time of the start of the reaction. Alternatively, the step (A) can be started under conditions where the mutant GSHB and/or Gly does not coexist in the reaction system, and the step (B) can be started by making the mutant GSHB and/or Gly coexist in the reaction system while the step (A) is in progress or after the step (A) is completed. Furthermore, γ-Glu-Val generated in the step (A) may be collected, and the step (B) may be carried out by using the collected γ-Glu-Val. γ-Glu-Val may be subjected to such a treatment as purification, dilution, concentration, drying, and dissolution, as required, and then used for the step (B).

Also, in the present invention, a reaction of Glu, Val, and Gly can be carried out to generate γ-Glu-Val-Gly by using the GSHA and the mutant GSHB. That is, another embodiment of the method for producing γ-Glu-Val-Gly of the present invention (enzymatic method) (it is also referred to as the "second embodiment") is a method for producing γ-Glu-Val-Gly, which comprises (C) a step of allowing the GSHA and the mutant GSHB to act on Glu, Val, and Gly to generate γ-Glu-Val-Gly. In the second embodiment, by making the GSHA, the mutant GSHB, Glu, Val, and Gly coexist in a reaction system, the GSHA and the mutant GSHB can be made to act on all of Glu, Val, and Gly to produce γ-Glu-Val-Gly.

The mode of the enzymes used for the method of the present invention is as described above. That is, as each enzyme, for example, a purified enzyme, any fraction containing the enzyme, or a combination of them can be used. As each enzyme, one kind of enzyme may be used, or two or more kinds of enzymes may be used in combination.

The enzymatic reaction can be attained by making the enzyme and the substrates coexist in a reaction mixture. That is, the enzymatic reaction can be carried out in an appropriate reaction mixture. The enzymatic reaction may be carried out by the batch method or the column method. When the batch method is used, the enzymatic reaction can be carried out by mixing the enzyme and the substrates in a reaction mixture contained in a reaction vessel. The enzymatic reaction may be carried out in a stationary state, or with stirring or shaking. When the column method is used, the enzymatic reaction can be carried out by passing a reaction mixture containing the substrates thorough a column filled with immobilized cells or immobilized enzyme. As the reaction mixture, water, buffer, or the like containing required ingredients can be used. The reaction mixture may contain, for example, the enzyme(s), substrates, ATP, and divalent metal ions. Combination of the ingredients used for the enzymatic reaction can be appropriately chosen according to type and implementation scheme of the step to be carried out, such as whether two or more of steps are simultaneously carried out or not.

The GSHA and the mutant GSHB each use ATP for the enzymatic reaction. Therefore, ATP is supplied to the reaction system as required. That is, the reaction system (reaction mixture) may contain ATP. The steps (A) to (C) each can be carried out in the presence of ATP. The method for supplying ATP is not particularly limited so long as ATP can be used for the enzymatic reaction. ATP can be added to the reaction mixture in any form, for example, in the form of powder or aqueous solution. ATP may also be supplied to the reaction system by, for example, a method for generating or regenerating ATP. As the method for generating or regenerating ATP, there are known the method of supplying ATP from a carbon source by using a *Corynebacterium* bacterium (Hori, H. et al., Appl. Microbiol. Biotechnol., 48(6):693-698 (1997)), the method of regenerating ATP by using yeast cells and glucose (Yamamoto, S et al., Biosci. Biotechnol. Biochem., 69(4):784-789 (2005)), the method of regenerating ATP using phosphoenolpyruvic acid and pyruvate kinase (C. Aug'e and Ch. Gautheron, Tetrahedron Lett., 29:789-790 (1988)), the method of regenerating ATP by using polyphosphoric acid and polyphosphate kinase (Murata, K. et al., Agric. Biol. Chem., 52(6):1471-1477 (1988)), and so forth. Examples of the polyphosphate kinase include, for example, polyphosphate kinase derived from *Sinorhizobium meliloti*, polyphosphate kinase derived from *Escherichia coli*, and polyphosphate kinase derived from *Corynebacterium glutamicum*.

Also, for example, the GSHA and the mutant GSHB each typically require a divalent metal ion for the enzymatic reaction. Therefore, the reaction system (reaction mixture) may contain a divalent metal ion. The steps (A) to (C) each can be carried out in the presence of a divalent metal ion. Examples of the divalent metal ion include $Mg^{2+}$ and $Mn^{2+}$, and preferred examples of the divalent metal ion include $Mg^{2+}$. The concentration of the divalent metal ion may be, for example, 1 to 200 mM.

Reaction conditions (pH of the reaction mixture, reaction temperature, reaction time, concentrations of various ingredients such as substrates and enzyme, etc.) are not particularly limited so long as γ-Glu-Val-Gly is generated.

The pH of the reaction mixture may be, for example, usually 6.0 to 10.0, preferably 6.5 to 9.0.

The reaction temperature may be, for example, usually 15 to 50° C., preferably 15 to 45° C., more preferably 20 to 40° C.

The reaction time may be, for example, 5 minutes to 200 hours for each of the steps (A) and (B) of the first embodiment. The reaction time may be, for example, 5 minutes to 200 hours for the step (C) of the second embodiment. Flow rate of the reaction mixture may be, for example, such a rate that the reaction time should be within the range of the reaction time exemplified above.

The concentration of each of the substrates in the reaction mixture may be, for example, usually 0.1 to 2000 mM, preferably 1 to 2000 mM, more preferably 10 to 1000 mM.

Molar ratio of the substrates in the reaction mixture for the step (A) of the first embodiment may be set so that, for example, usually, Glu:Val:ATP is 1:1:1, and ratio of any chosen substrate may be changed within the range of 0.1 to 10. That is, for example, Glu:Val:ATP may be 0.1 to 10:0.1 to 10:0.1 to 10. As for the step (B) of the first embodiment, the molar ratio of the substrates in the reaction mixture may be set so that, for example, usually, γ-Glu-Val:Gly:ATP is 1:1:1, and ratio of any chosen substrate may be changed within the range of 0.1 to 10. That is, for example, γ-Glu-Val:Gly:ATP may be 0.1 to 10:0.1 to 10:0.1 to 10. Molar ratio of the substrates in the reaction mixture for the step (C) of the second embodiment may be set so that, for example, usually, Glu:Val:Gly:ATP is 1:1:1:2, ratio of any chosen substrate may be changed within the range of 0.1 to 10, and ratio of ATP may be changed within the range of 0.2 to 20. That is, for example, Glu:Val:Gly:ATP may be 0.1 to 10:0.1 to 10:0.1 to 10:0.2 to 20. When the step (A) and the step (B) are simultaneously carried out in the first embodiment, molar ratio of the substrates in the first embodiment may be determined with reference to the molar ratio of the substrates for the second embodiment, as required.

The amount of the enzyme to be used can be set on the basis of, for example, enzymatic activity. The amount of the GSHA to be used may be, for example, usually 0.01 to 1000 U, preferably 0.1 to 500 U, more preferably 0.1 to 100 U, in terms of the γ-Glu-Val synthesis activity, to 1 mmol of the total amount of Glu and Val. As for the step (B) of the first embodiment, the amount of the mutant GSHB to be used may be, for example, usually 0.01 to 1000 U, preferably 0.1 to 500 U, more preferably 0.1 to 100 U, in terms of the γ-Glu-Val-Gly synthesis activity, to 1 mmol of the total amount of γ-Glu-Val and Gly. As for the step (C) of the second embodiment, the amount of the mutant GSHB to be used may be, for example, usually 0.01 to 1000 U, preferably 0.1 to 500 U, more preferably 0.1 to 100 U, in terms of the γ-Glu-Val-Gly synthesis activity, to 1 mmol of the total amount of a half of the amount of Glu, a half of the amount of Val, and the whole amount of Gly. When the step (A) and the step (B) are simultaneously carried out in the first embodiment, the amount of the mutant GSHB to be used in the first embodiment may be determined with reference to the amount of the mutant GSHB to be used in the second embodiment, as required.

In any of the embodiments, in the course of the enzymatic reaction, the substrates, enzymes, and/or other ingredients may be additionally added to the reaction system independently or in any combination. These ingredients may be added at one time, or two or more times, or they may be continuously added. The reaction conditions may be constant from the start to the end of the enzymatic reaction, or may change in the course of the enzymatic reaction. The expression "the reaction conditions change in the course of the enzymatic reaction" is not limited to cases where the reaction conditions temporally change, but also includes cases where the reaction conditions spatially change. The expression that "the reaction conditions spatially change" means that, for example, when the enzymatic reaction is carried out by the column method, the reaction conditions such as reaction temperature and enzyme concentration are different depending on the position on the flowing pathway.

By carrying out the enzymatic reaction as described above, a reaction mixture containing γ-Glu-Val-Gly can be obtained. Generation of γ-Glu-Val-Gly can be confirmed by a known technique used for detection or identification of a compound. Examples of such a technique include, for example, HPLC, LC/MS, GC/MS, and NMR. Any one of these techniques may be independently used, or two or more of them may be used in combination as required. γ-Glu-Val-Gly can be collected from the reaction mixture as required. γ-Glu-Val-Gly can be collected by a known technique used for separation and purification of a compound. Examples of such a technique include, for example, various chromatography techniques such as ion exchange chromatography, reverse phase high performance liquid chromatography, and affinity chromatography, as well as crystallization and recrystallization from a solution. Any one of these techniques may be independently used, or two or more of them may be used in combination as required. The collected γ-Glu-Val-Gly may contain ingredients other than γ-Glu-Val-Gly, such as ingredients used for the production of γ-Glu-Val-Gly and moisture. γ-Glu-Val-Gly may be purified to a desired extent. γ-Glu-Val-Gly may be purified to a purity of, for example, 30% (w/w) or higher, 50% (w/w) or higher, 70% (w/w) or higher, 80% (w/w) or higher, 90% (w/w) or higher, or 95% (w/w) or higher. Also, γ-Glu-Val can be collected in a manner similar to that for the collection of γ-Glu-Val-Gly.

<4-2> Fermentative Method

The present invention provides a method for producing γ-Glu-Val-Gly by fermentation using the mutant GSHB. Specifically, the present invention provides a method for producing γ-Glu-Val-Gly by fermentation using a microorganism having the mutant GSHB. This method is also referred to as "method for producing γ-Glu-Val-Gly of the present invention (fermentative method)".

In the present invention, γ-Glu-Val-Gly can be produced from γ-Glu-Val and Gly by fermentation using a microorganism having the mutant GSHB. That is, an embodiment of the method for producing γ-Glu-Val-Gly of the present invention (fermentative method) (also referred to as "third embodiment") is a method for producing γ-Glu-Val-Gly, which comprises (B) a step of culturing a microorganism having the mutant GSHB in a culture medium to generate γ-Glu-Val-Gly from γ-Glu-Val and Gly.

The third embodiment may further comprise (A) a step of generating γ-Glu-Val. In this case, γ-Glu-Val generated in the step (A) can be used as γ-Glu-Val in the step (B). That is, the third embodiment may be, for example, a method for producing γ-Glu-Val-Gly, which comprises (A) a step of generating γ-Glu-Val, and (B) a step of culturing a microorganism having the mutant GSHB in a culture medium to generate γ-Glu-Val-Gly from γ-Glu-Val generated in the step (A) and Gly. The step (A) can be carried out by such a method as described above. The step (A) may be, for example, a step of allowing the GSHA to act on Glu and Val to generate γ-Glu-Val, or a step of culturing a microorganism having the GSHA in a culture medium to generate γ-Glu-Val from Glu and Val. The third embodiment may specifically be, for example, a method for producing γ-Glu-Val-Gly, which comprises (A) a step of culturing a microorganism having the GSHA in a culture medium to generate γ-Glu-Val from Glu and Val, and (B) a step of culturing a microorganism having the mutant GSHB in a culture medium to generate γ-Glu-Val-Gly from γ-Glu-Val generated in the step (A) and Gly. Although the third embodiment is explained hereinafter with assuming a case where the step (A) is a step of culturing a microorganism having the GSHA in a culture medium to generate γ-Glu-Val from Glu and Val, the explanation can also be applied *mutatis mutandis* to cases of carrying out the step (A) by other methods.

In the third embodiment, the step (A) and the step (B) may be carried out separately, or may be carried simultaneously during a partial period or the whole period of the steps. That is, for example, the step (A) and the step (B) may be started simultaneously, or the step (B) may be started while the step (A) is in progress or after the step (A) is completed. In the third embodiment, the step (A) and the step (B) may be carried out by using a microorganism having the GSHA and another microorganism having the mutant GSHB, or may be carried out by using a single kind of microorganism having both the GSHA and the mutant GSHB. For example, if a microorganism having both the GSHA and the mutant GSHB is used, and it is cultured in a state that Glu, Val, and Gly are available, the step (A) and the step (B) can be simultaneously carried out. Furthermore, γ-Glu-Val generated in the step (A) may be collected, and added to a culture medium to carry out the step (B). γ-Glu-Val may be subjected to such a treatment as purification, dilution, concentration, drying, and dissolution, as required, and then used for the step (B).

Also, in the present invention, γ-Glu-Val-Gly can be produced by fermentation from Glu, Val, and Gly by using a microorganism having both the GSHA and the mutant GSHB. That is, another embodiment of the method for producing γ-Glu-Val-Gly of the present invention (fermentative method) (also referred to as "fourth embodiment") is a method for producing γ-Glu-Val-Gly, which comprises (C) a step of culturing a microorganism having the GSHA and the mutant GSHB in a culture medium to generate γ-Glu-Val-Gly from Glu, Val, and Gly.

The method for supplying amino acids used as the substrates is not particularly limited so long as the amino acids can be used for the enzymatic reaction. For example, the amino acids each may be biosynthesized by a microorganism used in the corresponding step, may be added to the culture medium, or may be supplied by a combination of the foregoing means. That is, for example, all of Glu, Val, and Gly may be biosynthesized by a microorganism, or all of Glu, Val, and Gly may be added to the culture medium. Alternatively, for example, one or two kinds of amino acids among Glu, Val, and Gly may be biosynthesized by a microorganism, and the other amino acid(s) may be added to the culture medium. All of Glu, Val, and Gly may also be biosynthesized by a microorganism, and added to the culture medium.

That is, an embodiment of the third embodiment may be, for example, a method for producing γ-Glu-Val-Gly, which comprises (B1) a step of culturing a microorganism having the mutant GSHB in a culture medium containing γ-Glu-Val and Gly to generating γ-Glu-Val-Gly, or a method for producing γ-Glu-Val-Gly, which comprises (B2) a step of culturing a microorganism having the mutant GSHB and having an ability to produce Gly in a culture medium containing γ-Glu-Val to generating γ-Glu-Val-Gly.

Also, an embodiment of the third embodiment may be, for example, a method for producing γ-Glu-Val-Gly, which comprises the step of (A1) or (A2), and the step of (B1) or (B2):

(A1) a step of culturing a microorganism having the GSHA in a culture medium containing Glu and Val to generate γ-Glu-Val;

(A2) a step of culturing a microorganism having the GSHA and having an ability to produce Glu and Val in a culture medium to generate γ-Glu-Val;

(B1) a step of culturing a microorganism having the mutant GSHB in a culture medium containing γ-Glu-Val generated in the step (A1) or (A2), and Gly to generating γ-Glu-Val-Gly;

(B2) a step of culturing a microorganism having the mutant GSHB and having an ability to produce Gly in a culture medium containing γ-Glu-Val generated in the step (A1) or (A2) to generating γ-Glu-Val-Gly.

Furthermore, an embodiment of the fourth embodiment may be, for example, a method for producing γ-Glu-Val-Gly, which comprises (C1) a step of culturing a microorganism having the GSHA and the mutant GSHB in a culture medium containing Glu, Val, and Gly to generating γ-Glu-Val-Gly, or a method for producing γ-Glu-Val-Gly, which comprises (C2) a step of culturing a microorganism having the GSHA and the mutant GSHB and having an ability to produce Glu, Val, and Gly in a culture medium to generating γ-Glu-Val-Gly.

As the microorganism having the GSHA, such a microorganism having the GSHA gene as mentioned above can be used as it is, or after modification as required. As the microorganism having the mutant GSHB, such a microorganism having the mutant GSHB gene as mentioned above can be used as it is, or after modification as required. As the microorganism having the GSHA and the mutant GSHB, such a microorganism having the GSHA gene and the mutant GSHB gene as mentioned above can be used as it is, or after modification as required.

The microorganism having an ability to produce an amino acid may be one inherently having the ability to produce an amino acid, or may be one modified to have the ability to produce an amino acid. A microorganism having an ability to produce an amino acid can be obtained by imparting an amino acid-producing ability to a microorganism, or by enhancing an amino acid-producing ability of a microorganism. Either the impartation or enhancement of an enzyme-producing ability, such as introduction of the GSHA gene and/or the mutant GSHB gene, or impartation or enhancement of an amino acid-producing ability may be carried out first. That is, a microorganism having the GSHA and/or the mutant GSHB and having an ability to produce an amino acid may be obtained by modifying a microorganism having the GSHA and/or the mutant GSHB so as to have an amino acid-producing ability, or may be obtained by modifying a microorganism having an amino acid-producing ability so as to have the GSHA and/or the mutant GSHB. An L-amino acid-producing ability can be imparted or enhanced by methods conventionally employed in the breeding of amino acid-producing strains of coryneform bacteria, Escherichia bacteria, and so forth (see "Amino Acid Fermentation", Gakkai Shuppan Center Ltd., 1st Edition, published May 30, 1986, pp. 77-100). Such methods include, for example, acquiring an auxotrophic mutant strain, an L-amino acid analogue-resistant strain, or a metabolic regulation mutant strain, and constructing a recombinant strain in which the activity of an L-amino acid biosynthesis system enzyme is enhanced. An L-amino acid-producing ability can also be imparted or enhanced by reducing the activity of an enzyme that catalyzes a reaction branching away from biosynthetic pathway of a target L-amino acid to generate a compound other than the target L-amino acid. The term "an enzyme that catalyzes a reaction branching away from the biosynthetic pathway of an objective L-amino acid to generate a compound other than the objective L-amino acid" referred to herein also includes an enzyme involved in decomposition of the objective amino acid.

Examples of L-glutamic acid biosynthesis enzymes include, for example, glutamate dehydrogenase (gdhA), glutamine synthetase (glnA), glutamate synthase (gltBD), isocitrate dehydrogenase (icdA), aconitate hydratase (acnA, acnB), citrate synthase (gltA), methylcitrate synthase (prpC), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), glucose phosphate isomerase (pgi), 6-phosphogluconate dehydratase (edd), 2-keto-3-deoxy-6-phosphogluconate aldolase (eda), and transhydrogenase. Examples of enzymes that catalyze a reaction branching away from the biosynthesis pathway of L-glutamic acid to generate a compound other than L-glutamic acid include, for example, isocitrate lyase (aceA), α-ketoglutarate dehydrogenase (sucA, odhA), acetolactate synthase (ilvI), formate acetyltransferase (pfl), lactate dehydrogenase (ldh), alcohol dehydrogenase (adh), glutamate decarboxylase (gadAB), and succinate dehydrogenase (sdhABCD). Shown in the parentheses after the names of the enzymes are examples of genes encoding the enzymes (the same shall apply to the same occasions hereinafter). Specific examples of L-glutamic acid-producing bacteria include a recombinant strain obtained by introducing the mviN gene having V197M mutation into an odhA-deficient strain obtained from the Corynebacterium glutamicum (Brevibacterium lactofermentum) ATCC 13869 strain (Japanese Patent Laid-open (Kokai) No. 2010-161970), the Pantoea agglomerans AJ13355 strain introduced with the gltA (citrate synthase) gene derived from Brevibacierium lactofermentum (Japanese Patent No. 4285582), and an Escherichia bacterium having a mutant glutamine synthetase in which the tyrosine residue at position 397 is replaced with another amino acid residue (U.S. Patent Published Application No. 2003/0148474).

Examples of L-valine biosynthesis enzymes include, for example, the enzymes encoded by the ilvGMED genes of the ilvGMEDA operon and the enzymes encoded by the genes of the ilvBNC operon. The ilvGM genes encode acetohydroxy acid synthase isozyme II (AHAS II), the ilvE gene encodes transaminase, and the ilvD gene encodes dihydroxy-acid dehydratase. The ilvBN gene encodes acetohydroxy acid synthase, and the ilvC gene encodes isomeroreductase (WO00/50624). Expressions of the ilvGMEDA operon and the ilvBNC operon are suppressed (attenuated) by L-valine, L-isoleucine, and/or L-leucine. Therefore, for enhancing the activity of such an enzyme, it is preferred that the suppression of expression by the produced L-valine is released by removing or modifying a region required for the attenuation. Furthermore, threonine deaminase encoded by the ilvA gene is an enzyme that catalyzes the deamination reaction of L-threonine resulting 2-ketobutyric acid, which is the rate-limiting step of the L-isoleucine biosynthesis system. Therefore, when using the ilvGMEDA operon, it is preferred that the operon is used after disrupting or deleting the ilvA gene so that no functional threonine deaminase is expressed. Examples of enzymes that catalyze a reaction branching away from the biosynthesis pathway of L-valine to generate a compound other than L-valine include, for example, threonine deaminase (ilvA) involved in the L-isoleucine biosynthesis, and enzymes (panB, panC) involved in the D-pantothenic acid biosynthesis (WO00/50624). Specific examples of L-valine-producing bacteria include the Escherichia coli VL1970 strain (U.S. Pat. No. 5,658,766), an Escherichia bacterium having a mutation for requiring lipoic acid for growth thereof and/or a mutation for lacking H$^+$-ATPase, and an Escherichia bacterium having these characteristics and introduced with the ilvGMEDA operon that expresses at least the ilvG, ilvM, ilvE, and ilvD genes, but does not express any functional threonine deaminase (WO96/06926).

Furthermore, examples of methods for imparting or enhancing an L-amino acid-producing ability also include, for example, a method of modifying a bacterium so that the bacterium has an increased activity or activities of one or more proteins selected from proteins involved in the glycometabolism and proteins involved in the energy metabolism.

That is, for example, by introducing any of these modifications into a microorganism, an amino acid-producing ability can be imparted or enhanced. All of these modifications may be used independently or in any appropriate combination.

The microorganism may also have been modified so that the ability to uptake an amino acid added to the culture medium is improved. The microorganism may also have been modified so that the ability to excrete the generated γ-Glu-Val out of the cell is improved, or it may have been modified so that the ability to uptake γ-Glu-Val added to the culture medium is improved, depending on the scheme of use of the microorganism. The microorganism may also have been modified so that the ability to excrete the generated γ-Glu-Val-Gly out of the cell is improved.

Culture conditions are not particularly limited, so long as the microorganism can proliferate, and γ-Glu-Val-Gly is generated. Regarding the culture conditions, the descriptions concerning the culture conditions in the method for producing the mutant GSHB mentioned above can be used as a reference.

The GSHA and the mutant GSHB each use ATP for the enzymatic reaction. Therefore, ATP is supplied to the reaction system as required. That is, the reaction system may contain ATP. The steps (A) to (C) each can be carried out in the presence of ATP. The method for supplying ATP is not particularly limited so long as ATP can be used for the enzymatic reaction. ATP may be, for example, generated by a microorganism used in each step, or supplied to the reaction system by such a method for generating or regenerating ATP as mentioned above. For supplying ATP, for example, there can be preferably used a co-culture system such as those realized by a method of making a microorganism of which ATP regenerating system based on the usual energy metabolism is enhanced, or a microorganism having an ability to regenerate ATP by the action of polyphosphate kinase coexist in the culture medium (Japanese Patent Publication (Kokoku) Nos. 7-16431 and 6-69386).

Also, for example, the GSHA and the mutant GSHB each typically require a divalent metal ion for the enzymatic reaction. Therefore, the reaction system may contain a divalent metal ion. The steps (A) to (C) each can be carried out in the presence of a divalent metal ion.

When a culture medium containing an amino acid is used, the amino acid may be contained in the culture medium from the start of the culture, or may be added to the culture medium at any time during the culture. Although the time of the addition can be changed as required according to various conditions such as culture time, the amino acid may be added, for example, preferably 0 to 50 hours, more preferably 0.1 to 24 hours, particularly preferably 0.5 to 6 hours, before the end of the culture. The amino acid may be added at one time, or two or more times, or it may be continuously added. The concentration of each of the amino acids in the culture medium may be, for example, usually 0.1 to 2000 mM, preferably 1 to 2000 mM, more preferably 10 to 1000 mM. As for molar ratio of substrates in the culture medium, the descriptions concerning the molar ratio of substrates in the reaction mixture for the enzymatic method may be applied *mutatis mutandis*.

By carrying out culture as described above, a culture broth containing γ-Glu-Val-Gly can be obtained. Generation of γ-Glu-Val-Gly can be confirmed by a known technique used for detection or identification of a compound as described above. γ-Glu-Val-Gly can be collected from the culture broth as required. γ-Glu-Val-Gly can be collected by a known technique used for separation or purification of a compound as described above. When γ-Glu-Val-Gly is accumulated in the cells, for example, the cells can be disrupted by ultrasonication or the like, and γ-Glu-Val-Gly can be collected by the ion-exchange resin method or the like from supernatant obtained by removing the cells by centrifugation.

When the microorganism having the mutant GSHB is yeast, and γ-Glu-Val-Gly is accumulated in the cells thereof, this yeast can be used for, for example, production of yeast extract containing γ-Glu-Val-Gly. That is, the present invention provides a method for producing yeast extract containing γ-Glu-Val-Gly, which comprises preparing yeast extract by using the yeast as a raw material. The yeast extract can be prepared from the yeast in the same manner as usual production of yeast extract. The yeast extract may be one obtained by hot water extraction of the yeast cells followed by treatment of the resulting extract, or one obtained by digestion of the yeast cells followed by treatment of the digested product. The obtained yeast extract may be concentrated, or may be dried to make it in the form of powder, as required.

EXAMPLES

Hereinafter, the present invention will be more specifically explained with reference to non-limiting examples.

[Example 1] Construction of Expression Plasmid for Wild-Type gshB Gene

*Escherichia coli* BL21(DE3) (Life Technologies) was transformed with pET-gshB (Japanese Patent Laid-open (Kokai) No. 2012-85637), which is an expression plasmid for the gshB gene (SEQ ID NO: 1) of *Escherichia coli* W3110 (ATCC 27325) encoding glutathione synthetase, to obtain *Escherichia coli* BL21(DE3)/pET-gshB. The nucleotide sequence of the gshB gene and the amino acid sequence of the GSHB encoded by that gene are shown as SEQ ID NOS: 1 and 2, respectively. With pET-gshB, the GSHB is expressed with a His tag added to the C-terminus.

[Example 2] Construction of Expression Plasmids for Mutant gshB Genes

In order to construct mutant gshB genes, PCR was performed by using the primers corresponding to the respective mutant gshB genes (SEQ ID NOS: 3 to 18) and pET-gshB described in Example 1 as the template with Quik Change Site-Directed Mutagenesis Kit (Stratagene) according to the protocol of the manufacturer. The relations between the mutations and the primers are shown in Table 1. In the table, the sequences indicated with capital letters correspond to the amino acid residues for which a mutation was introduced.

Each of the obtained PCR products was digested with DpnI, and *Escherichia coli* JM109 was transformed with the digestion reaction mixture, applied to the LB agar medium containing 100 μg/mL of ampicillin sodium salt (Amp), and cultured at 30° C. for 20 hours. Plasmids were extracted from the colonies of the grown transformants by a known method, the nucleotide sequences thereof were confirmed by using 3130 Genetic Analyzer (Life Technologies), and a plasmid having the objective structure was obtained as an expression plasmid for the mutant gshB gene. Then, *Escherichia coli* BL21(DE3) (Life Technologies) was transformed with the obtained plasmid. With pET21-EcGshB, the GSHB is expressed with a His tag added to the C-terminus, and therefore, with these expression plasmids for the mutant gshB genes, the GSHBs are also expressed with a His tag added to the C-terminus.

TABLE 1

| SEQ ID NO | Primer sequence (5'→3') | Introduced mutation |
|---|---|---|
| 3 | accagcGTGacctgtattcgtgagatt | P287V |
| 4 | acaggtCACgctggtgacgttaatttc | |
| 5 | gacggtTGCggcggcgcgtcgattttc | M165C |
| 6 | gccgccGCAaccgtccagcggcttaag | |
| 7 | gacggtTTTggcggcgcgtcgattttc | M165F |
| 8 | gccgccAAAaccgtccagcggcttaag | |
| 9 | gacggtTGGggcggcgcgtcgattttc | M165W |
| 10 | gccgccCCAaccgtccagcggcttaag | |
| 11 | gacggtGCGggcggcgcgtcgattttc | M165A |
| 12 | gccgccCGCaccgtccagcggcttaag | |
| 13 | aagccgctggacggtAGCggcggcgcgtcgatt | M165S |
| 14 | aatcgacgcgccgccGCTaccgtccagcggctt | |
| 15 | aagccgctggacggtCATggcggcgcgtcgatt | M165H |
| 16 | aatcgacgcgccgccATGaccgtccagcggctt | |
| 17 | aagccgctggacggtGGCggcggcgcgtcgatt | M165G |
| 18 | aatcgacgcgccgccGCCaccgtccagcggctt | |

[Example 3] Purification of GSHBs Derived from *Escherichia coli* W3110, Having His Tag Added to C-Terminus Each of the strains obtained in Examples 1 and 2 (i.e. *Escherichia coli* BL21(DE3) strains harboring the respective gshB gene expression plasmids) was inoculated into 3 mL of the LB medium (1.0% (w/v) peptone, 0.5% (w/v) yeast extract, 1.0% (w/v) NaCl) containing 100 µg/mL of Amp, and cultured at 30° C. for 20 hours with shaking by 120 times/minute of reciprocal movement to obtain a preculture broth. The obtained preculture broth in a volume of 150 µl was inoculated into 15 mL of Overnight Express Instant TB medium (Novagen) containing 100 µg/mL of Amp contained in a 70 mL-volume test tube ((φ25 mm). Culture was performed at 30° C. for 20 hours with shaking by 120 times/minute of reciprocal movement, and then the cells were collected by centrifugation (4° C., 12,000 rpm, 5 minutes). The cells obtained as precipitates were suspended in 0.2 mL of a buffer (20 mM Tris-HCl (pH 8.0), 300 mM NaCl, 10 mM imidazole, and 15% glycerol), and disrupted by ultrasonication with cooling. The obtained disrupted cell suspension was centrifuged (4° C., 29,100×g, 10 minutes), and the obtained supernatant was used as a cell-free extract.

The obtained cell-free extract was applied to Nickel Sepharose 6 Fast Flow Beads (GE Healthcare) equilibrated beforehand with a buffer (20 mM Tris-HCl (pH 8.0), 300 mM NaCl, 10 mM imidazole, and 15% glycerol), and the enzyme was eluted with an elution buffer (20 mM Tris-HCl (pH 8.0), 300 mM NaCl, 250 mM imidazole, and 15% glycerol) to obtain an active fraction. This active fraction was used as a purified GSHB for the following experiments.

[Example 4] Generation of γ-Glu-Val-Gly Using Each Purified GSHB

The synthesis activity of γ-Glu-Val-Gly (CAS 38837-70-6; also referred to as "Gluvalicine") was measured for each of the purified GSHBs obtained in Example 3.

The measurement conditions for the γ-Glu-Val-Gly synthesis activity were as follows. The composition of the reaction mixture consisted of 10 mM γ-Glu-Val, 150 mM glycine, 10 mM ATP, and 10 mM $MgSO_4$ in 100 mM Tris-HCl (pH 9.0). The volume of the reaction mixture was 0.2 mL, and the enzymatic reaction was started by adding the purified enzyme. The purified GSHB was added to reaction mixture at a concentration of 0.025 mg/mL. The reaction temperature was 30° C., and the reaction time was 30 minutes. For terminating the reaction, 0.2 mL of 200 mM sulfuric acid was added per 0.2 mL of the reaction mixture. After completion of the reaction, the generated γ-Glu-Val-Gly was quantified by HPLC.

The quantification conditions for γ-Glu-Val-Gly were as follows. Synergi 4 µl Hydro-RP 80A produced by Phenomenex (particle size 4 microns, inner diameter 4.6 mm, length 250 mm) was used as the column. As the eluent, a mixture consisting of 50 mM sodium dihydrogenphosphate (pH 2.5, adjusted with phosphoric acid) and 3.5% (v/v) acetonitrile was used. The flow rate was 1.0 mL/minute, column temperature was 40° C., and UV detection wavelength was 210 nm.

The generation amount of γ-Glu-Val-Gly was quantified by the aforementioned method, and the specific activity was calculated. The results are shown in Table 2. The term "GSHB-WT" mentioned in the table represents the wild-type GSHB. One enzyme unit (U) represents an amount of enzyme that generates 1 µmol of γ-Glu-Val-Gly in 1 minute under the aforementioned conditions.

TABLE 2

| Mutation | γ-Glu-Val-Gly synthesis activity (U/mg) |
|---|---|
| GSHB-WT | 2.25 |
| P287V | 2.82 |
| M165C | 4.33 |
| M165F | 3.76 |
| M165W | 3.00 |
| M165A | 3.02 |
| M165S | 4.02 |
| M165H | 4.75 |
| M165G | 3.22 |

[Example 5] Acquisition of Purified GSHB Derived from *Escherichia coli* W3110 Having His Tag Added to C-Terminus Using Cell-Free Protein Synthesis System Purified enzymes of the wild-type GSHB and mutant GSHBs derived from the *Escherichia coli* W3110 (ATCC 27325) were obtained by entrusting the preparation thereof to the cell-free protein synthesis service of the independent administrative agency, Institute of Physical and Chemical Research (RIKEN) (www(dot)ynmr(dot)riken(dot)jp/apply_ inform/fee(dot)html), and used in the following experiments. Eluted fractions obtained by affinity purification of the synthesized proteins using nickel were used as purified enzymes. For the elution, a buffer (50 mM sodium phosphate buffer (pH 8.0), 10% glycerol, 300 mM imidazole, 300 mM NaCl, 1 mM DTT) was used. Since the start codon of these genes was TTG, the start codon was replaced with ATG at the time of the synthesis of the proteins. The wild-type GSHB and mutant GSHBs were expressed with 6 His residues added to the C-terminus. At the time of the protein synthesis, the expression amount improvement option of the cell-free protein synthesis service was used.

[Example 6] Generation of γ-Glu-Val-Gly Using Each Purified GSHB Synthesized in Cell-Free Protein Synthesis System The γ-Glu-Val-Gly synthesis activity was measured for each of the purified GSHBs obtained in Example 5.

The measurement conditions for the γ-Glu-Val-Gly synthesis activity were as follows. The composition of the reaction mixture consisted of 10 mM γ-Glu-Val, 10 mM glycine, 10 mM ATP, and 10 mM $MgSO_4$ in 100 mM Tris-HCl (pH 9.0). The volume of the reaction mixture was 0.1 mL, and the enzymatic reaction was started by adding the purified enzyme. The purified GSHB was added to the reaction mixture at a concentration of 0.025 g/L. The reaction temperature was 30° C., and the reaction time was 30 minutes. For terminating the reaction, 0.1 mL of 200 mM sulfuric acid was added per 0.1 mL of the reaction mixture. After completion of the reaction, the generated γ-Glu-Val-Gly was quantified in the same manner as that described in Example 4, and the specific activity was calculated. The specific activity of the wild-type GSHB was calculated to be 0.34 U/mg at this time. One enzyme unit (U) represents an amount of enzyme that generates 1 μmol of γ-Glu-Val-Gly in 1 minute under the aforementioned conditions. The relative activity values of the respective mutant GSHBs to the wild-type are shown in Table 3. The term "GSHB-WT" mentioned in the table represents the wild-type GSHB.

TABLE 3

| Mutation | Relative γ-Glu-Val-Gly synthesis activity |
|---|---|
| GSHB-WT | 1 |
| M165H | 7.6 |
| Y200F | 3.0 |
| Y200H | 1.1 |
| N199A | 1.6 |
| N199G | 1.2 |
| T285S | 1.2 |
| M165H/V7I | 9.3 |
| M165H/N13K | 9.3 |
| M165H/I14V | 8.6 |
| M165H/N15K | 11 |
| M165H/N15H | 9.9 |
| M165H/K17Y | 8.9 |
| M165H/K17R | 8.4 |
| M165H/F22I | 9.2 |
| M165H/I274M | 8.5 |
| Y200F/M165S | 6.4 |
| Y200F/N199A | 4.7 |
| Y200F/N199G | 4.1 |
| Y200F/N199E | 3.6 |
| Y200F/P202A | 3.4 |
| Y200F/T285S | 3.3 |
| Y200F/F95L | 3.3 |

[Example 7] Construction of Host Having Improved Val-Producing Ability (*Escherichia coli* WY-01)

*Escherichia coli* K-12 MG1655 (ATCC 47076) was introduced with an ilvGMEDA operon (10 copies) and a scrKYABR operon (1 copy) by the Mini-Mu method (Elena G. Abalakina et. al., Appl Microbiol Biotechnol 81:191-200 (2008)), to construct a strain having an improved Val-producing ability (hereinafter also referred to as "strain WY-01"). The ilvGMEDA operon introduced was derived from *Escherichia coli*. As the ilvG gene in this operon, the ilvG603 gene (Japanese Patent Laid-open (Kokai) No. 2005-333984), of which frameshift mutation has been eliminated and thereby which expresses an active AHAS II, was used in order to avoid growth delay due to Val accumulation. The scrKYABR operon introduced was derived from a transposon Tn2555 (Japanese Patent Laid-open (Kokai) No. 2001-346578).

[Example 8] Construction of Expression Plasmid for KrgshA, pMW219-Plac-KrgshA

Synthesis of the γ-glutamylvaline synthetase gene derived from *Kocuria rosea* (hereinafter also referred to as "KrgshA") was outsourced to GenScript, and the gene was cloned into the XbaI site of the multiple cloning site of pMW219 (NIPPON GENE, Code No. 310-02571) by the In-Fusion method, to obtain an expression plasmid for KrgshA, pMW219-Plac-KrgshA. The start codon "gtg" of KrgshA was replaced with "atg". The nucleotide sequence of KrgshA is shown as SEQ ID NO: 21.

[Example 9] Construction of Expression Plasmid for Wild-Type gshB Gene, pUC19-Plac-gshB PCR was carried out by using the genome of *E. coli* K-12 MG1655 (ATCC 47076) as the template, and primers shown as SEQ ID NOS: 19 and 20. PCR conditions consisted of 25 cycles of denaturing (94° C. for 10 sec), annealing (55° C. for 10 sec), and extension (72° C. for 1 min). PCR was carried out using GeneAmp PCR System 9700. The obtained DNA fragment was introduced by the in-fusion cloning method into pUC19 linearized by digestion with a restriction enzyme XbaI, to obtain an expression plasmid for the wild-type gshB gene, pUC19-Plac-gshB.

TABLE 4

| SEQ ID NO | Primer sequence (5'→3') |
|---|---|
| 19 | gtacccggggatcctttactgctgctgtaaacgtg |
| 20 | gcctgcaggtcgactatgatcaagctcggcatcgt |

[Example 10] Construction of Expression Plasmids for Mutant gshB Genes

In order to construct mutant gshB genes, PCR was carried out by using pUC19-Plac-gshB constructed in Example 9 as the template, and primers for introducing mutations shown as SEQ ID NOS: 3 to 6. The relations between the mutations and the primers are shown in Table 1. PCR conditions consisted of 25 cycles of denaturing (94° C. for 10 sec), annealing (60° C. for 10 sec), and extension (72° C. for 4 min). PCR was carried out using GeneAmp PCR System 9700. Each of the obtained PCR products was digested with DpnI, and JM109 competent cells were transformed with the reaction mixture, to obtain expression plasmids for three mutant gshB genes. The notation "gshB*" indicates a gene introduced with a mutation.

[Example 11] Construction of *Escherichia coli* WY-01 Introduced with KrgshA Expression Plasmid pMW219-Plac-KrgshA and gshB Gene Expression Plasmid The strain WY-01 constructed in Example 7 was introduced with the expression plasmid for KrgshA, pMW219-Plac-KrgshA constructed in Example 8 by the transformation method. The obtained strain was further introduced with the expression plasmid for the wild-type gshB gene, pUC19-Plac-gshB, constructed in Example 9 or with each of the expression plasmids for mutant gshB genes constructed in Example 10 by the transformation method, to construct strains WY-01/pMW219-Plac-KrgshA, pUC19-Plac-gshB, WY-01/pMW219-Plac-KrgshA, pUC19-Plac-gshB*P287V, WY-01/pMW219-Plac-KrgshA, pUC19-Plat-gshB*M165F, and WY-01/pMW219-Plac-KrgshA, pUC19-Plat-gshB*M165F.

[Example 12] Verification of γ-Glu-Val-Gly Synthesis Activity of Mutant GSHBs in Bacterial Cells Culture evaluation of the strains constructed in Example 11 in flask system was carried out. Each strain grown on a plate was inoculated to 40 mL of MS-pyruvate medium (added with antibiotics such as Amp and Km as required) in a flask to obtain an OD600 of 0.2, and cultured (120 rpm, 30° C.). After culturing for 21.5 hours, the culture broth was sampled, and the glucose concentration was measured and confirmed to be 0 g/L. The medium was added with glucose to a final concentration of 10 g/L, IPTG to a final concentration of 1 mM, and Gly to a final concentration of 1 g/L. Then, after further culturing for 3.5 hours, the γ-Glu-Val-Gly concentration in the culture broth was analyzed. As a result, the γ-Glu-Val-Gly accumulation was increased by about 14% in the strain expressing the P287V mutant GSHB or by about 67% in the strain expressing the M165F or M165C mutant GSHB as compared with the strain expressing the wild-type GSHB (the drawing).

| <Composition of MS-pyruvate medium> | |
|---|---|
| [Group A] | |
| Glucose | 40.0 g/L |
| MgSO$_4$•7H$_2$O | 1.0 g/L |
| Not pH-adjusted, sterilized by autoclave at 115° C. for 15 minutes. | |
| [Group B] | |
| (NH$_4$)$_2$SO$_4$ | 24.0 g/L |
| KH$_2$PO$_4$ | 1.0 g/L |

| <Composition of MS-pyruvate medium> | |
|---|---|
| Yeast extract | 2.0 g/L |
| FeSO$_4$•7H$_2$O | 10.0 mg/L |
| MnSO$_4$•4H$_2$O | 8.0 mg/L |
| pH 7.0 (KOH), sterilized by autoclave at 115° C. for 15 minutes. | |
| [Group C] | |
| CaCO$_3$ | 50 g/L |
| Heat-sterilized at 180° C. | |

The groups A, B, and C were independently sterilized, and then mutually mixed. A 250 g/L solution (500-fold concentrate) of pyruvic acid was prepared and filter-sterilized, and added immediately before culturing to a final concentration of 500 mg/L.

INDUSTRIAL APPLICABILITY

According to the present invention, a mutant GSHB suitable for generating γ-Glu-Val-Gly is provided. In addition, according to the present invention, γ-Glu-Val-Gly can be efficiently produced by using the mutant GSHB.

Explanation of Sequence Listing

SEQ ID NOS:
1: Nucleotide sequence of gshB gene of *Escherichia coli* K-12 W3110
2: Amino acid sequence of GshB protein of *Escherichia coli* K-12 W3110
3 to 20: Primers
21: Nucleotide sequence of GSHA gene of *Kocuria rosea* AJ3132
22: Amino acid sequence of GSHA of *Kocuria rosea* AJ3132
23: Nucleotide sequence of GSHA gene of *Kocuria rhizophila* DC2201
24: Amino acid sequence of GSHA of *Kocuria rhizophila* DC2201
25: Nucleotide sequence of GSHA gene of *Micrococcus hueus* NCTC2665
26: Amino acid sequence of GSHA of *Micrococcus luteus* NCTC2665
27: Nucleotide sequence of gshA gene of *Escherichia coli* K-12 MG1655
28: Amino acid sequence of GshA protein of *Escherichia coli* K-12 MG1655
29: Nucleotide sequence of ggt gene of *Escherichia coli* K-12 MG1655
30: Amino acid sequence of Ggt protein of *Escherichia coli* K-12 MG1655

The invention claimed is:

1. A method for producing γ-Glu-Val-Gly and/or a salt thereof, the method comprising:
   reacting a mutant glutathione synthetase with γ-Glu-Val and Gly to generate γ-Glu-Val-Gly,
   wherein the mutant glutathione synthetase has γ-glutamylvalylglycine synthetase activity and comprises an amino acid sequence having at least 90% sequence identity to the amino acid sequence of SEQ ID NO: 2, where at least one amino acid residue in the mutant glutathione synthetase corresponding to the following amino acid residue (A) or (B) is mutated to a different amino acid:
   (A) at least one amino acid residue selected from the group consisting of F22, M165, I274, T285, and P287 in SEQ ID NO: 2;
   (B) a combination of at least one amino acid residue selected from the group consisting of V7, N13, I14, N15, K17, F95, N199, Y200, and P202 in SEQ ID NO:2 and the amino acid residue (A).

2. The method according to claim 1, wherein the at least one amino acid residue mutated in the mutant glutathione synthetase corresponds to mutations in the amino acid sequence of SEQ ID NO: 2 selected from the group consisting of:
   F22(I), M165(A, C, F, G, H, S, W), I274(M), T285(S), and P287(V).

3. The method according to claim 1, wherein the at least one amino acid residue mutated in the mutant glutathione synthetase corresponds to mutations in the amino acid sequence of SEQ ID NO: 2 selected from the group consisting of:
   M165H/V71, M165H/N13K, M165H/I14V, M165H/N15K, M165H/N15H, M165H/K17Y, M165H/K17R, M165H/F22I, M165H/I274M, Y200F/M165S, and Y200F/T285S.

4. The method according to claim 1, further comprising:
   reacting a γ-glutamylvaline synthetase with Glu and Val to generate γ-Glu-Val,
   wherein the generated γ-Glu-Val is reacted with the mutant glutathione synthetase.

5. The method according to claim 1, wherein the mutant glutathione synthetase is purified.

6. The method according to claim 1, wherein the mutant glutathione synthetase is immobilized.

7. The method according to claim 1, wherein the mutant glutathione synthetase is contained in a culture broth of a microorganism having the mutant glutathione synthetase, cultured cells of a microorganism having the mutant glutathione synthetase, or a processed product of the cultured cells of a microorganism having the mutant glutathione synthetase.

8. The method according to claim 4, wherein the γ-glutamylvaline synthetase is contained in a culture broth of a microorganism having the γ-glutamylvaline synthetase, cultured cells of a microorganism having the γ-glutamylvaline synthetase, or a processed product of the cultured cells of a microorganism having the γ-glutamylvaline synthetase.

9. The method according to claim 4, wherein the γ-glutamylvaline synthetase and the mutant glutathione synthetase are contained in a culture broth of a microorganism having the γ-glutamylvaline synthetase and the mutant glutathione synthetase, cultured cells of a microorganism having the γ-glutamylvaline synthetase and the mutant glutathione synthetase, or a processed product of the cultured cells of a microorganism having the γ-glutamylvaline synthetase and the mutant glutathione synthetase.

10. A method for producing γ-Glu-Val-Gly and/or a salt thereof, the method comprising:
    reacting a γ-glutamylvaline synthetase and a mutant glutathione synthetase with Glu, Val, and Gly to generate γ-Glu-Val-Gly,
    wherein the mutant glutathione synthetase has γ-glutamylvalylglycine synthetase activity and comprises an amino acid sequence having at least 90% sequence identity to the amino acid sequence of SEQ ID NO: 2, where at least one amino acid residue in the mutant glutathione synthetase corresponding to the following amino acid residue (A) or (B) is mutated to a different amino acid:
    (A) at least one amino acid residue selected from the group consisting of F22, M165, I274, T285, and P287 in ID NO: 2;

(B) a combination of at least one amino acid residue selected from the group consisting of V7, N13, I14, N15, K17, F95, N199, Y200, and P202 in SEQ ID NO: 2 and the amino acid residue (A).

11. A method for producing γ-Glu-Val-Gly and/or a salt thereof, the method comprising
culturing a microorganism having a mutant glutathione synthetase in a culture medium to generate γ-Glu-Val-Gly from γ-Glu-Val and Gly,
wherein the mutant glutathione synthetase has γ-glutamylvalylglycine synthetase activity and comprises an amino acid sequence having at least 90% sequence identity to the amino acid sequence of SEQ ID NO: 2, where at least one amino acid residue in the mutant glutathione synthetase corresponding to the following amino acid residue (A) or (B) is mutated to a different amino acid:
(A) at least one amino acid residue selected from the group consisting of F22, M165, I274, T285, and P287 in SEQ ID NO: 2;
(B) a combination of at least one amino acid residue selected from the group consisting of V7, N13, I14, N15, K17, F95, N199, Y200, and P202 in SEQ ID NO: 2 and the amino acid residue (A).

12. The method according to claim 11, further comprising:
culturing a microorganism in culture medium to generate γ-Glu-Val from Glu and Val, where the microorganism comprises γ-glutamylvaline synthetase,
wherein the generated γ-Glu-Val is included in the culture medium for culturing the microorganism having the mutant glutathione synthetase to generate γ-Glu-Val-Gly.

13. A method for producing γ-Glu-Val-Gly and/or a salt thereof, the method comprising:
culturing a microorganism in a culture medium to generate γ-Glu-Val-Gly from Glu, Val, and Gly, where the microorganism comprises γ-glutamylvaline synthetase and a mutant glutathione synthetase,
wherein the mutant glutathione synthetase has γ-glutamylvalylglycine synthetase activity and comprises an amino acid sequence having at least 90% sequence identity to the amino acid sequence of SEQ ID NO: 2, where at least one amino acid residue in the mutant glutathione synthetase corresponding to the following amino acid residue (A) or (B) is mutated to a different amino acid:
(A) at least one amino acid residue selected from the group consisting of F22, M165, I274, T285, and P287 in SEQ ID NO: 2;
(B) a combination of at least one amino acid residue selected from the group consisting of V7, N13, I14, N15, K17, F95, N199, Y200, and P202 in SEQ ID NO: 2 and the amino acid residue (A).

14. The method according to claim 7, wherein the microorganism has been modified so that the activity of γ-glutamyltransferase is reduced as compared with a corresponding non-modified microorganism.

15. The method according to claim 7, wherein the microorganism is *Escherichia coli*.

16. The method according to claim 1, wherein the reacting of the mutant glutathione synthetase with γ-Glu-Val and Gly is carried out in the presence of ATP.

17. The method according to claim 4, wherein the γ-glutamylvaline synthetase has γ-glutamylvaline synthetase activity and comprises an amino acid sequence having at least 90% sequence identity to the amino acid sequence of SEQ ID NO: 22, 24, or 26.

18. The method according to claim 4, wherein the γ-glutamylvaline synthetase is a mutant glutamte-cysteine ligase, and the mutant glutamate-cysteine ligase has γ-glutamylvaline synthetase activity and comprises an amino acid sequence having at least 90% sequence identity to the amino acid sequence of SEQ ID NO: 28, where at least one amino acid residue in the mutant glutamate-cysteine ligase corresponding to at least one amino acid residue selected from the group consisting of L135, Q144, Y241, N243, and Y300 in SEQ ID NO: 28 is mutated to a different amino acid.

19. The method according to claim 10, wherein the at least one amino acid residue is mutated in the mutant glutathione synthetase such that the mutation corresponds to at least one mutation in the acid sequence of SEQ ID NO: 2 selected from the group consisting of:
F22(I), M165(A, C, F, G, H, S, W), I274(M), T285(S), and P287(V).

20. The method according to claim 11, wherein the at least one amino acid residue is mutated in the mutant glutathione synthetase such that the mutation corresponds to at least one mutation in the amino acid sequence of SEQ ID NO: 2 selected from the group consisting of:
F22(I), M165(A, C, F, G, H, S, W), I274(M), T285(S), and P287(V).

21. The method according to claim 13, wherein the at least one amino acid residue is mutated in the mutant glutathione synthetase such that the mutation corresponds to at least one mutation in the amino acid sequence of SEQ ID NO: 2 selected front the group consisting of:
F22(I), M165(A, C, F, G, H, S, W), I274(M), T285(S), and P287(V).

22. The method according to claim 21, wherein the at least one amino acid residue is mutated in the mutant glutamate-cysteine ligase such that the mutation corresponds at least one mutation in the amino acid sequence of SEQ ID NO: 28 selected from the group consisting of:
L135(I, F, M, V, G, A, W, K, H, R, C, N, S, T),
Q144(F, A, N, S, D, T, R, H, G, K, Y, W, C, M, P, V, L, I),
Y241(A),
N243(I, W, K, R, H), and
Y300(A, H, R, K).

* * * * *